(12) United States Patent
Yoneda

(10) Patent No.: US 6,538,729 B2
(45) Date of Patent: Mar. 25, 2003

(54) UNIT FOR INSPECTING A SURFACE

(75) Inventor: Kenji Yoneda, Kyoto (JP)

(73) Assignee: CCS Co., Ltd., Kyoto (JP)

( * ) Notice: Subject to any disclaimer, the term of this patent is extended or adjusted under 35 U.S.C. 154(b) by 181 days.

(21) Appl. No.: 09/742,356

(22) Filed: Dec. 22, 2000

(65) Prior Publication Data

US 2001/0028452 A1 Oct. 11, 2001

(30) Foreign Application Priority Data

Apr. 10, 2000 (JP) ........................................ 2000-108677
May 19, 2000 (JP) ........................................ 2000-149049
Jun. 13, 2000 (JP) ........................................ 2000-177649

(51) Int. Cl.$^7$ ............................................. G01N 21/00
(52) U.S. Cl. ................................. 356/237.2; 356/237.1
(58) Field of Search ........................... 356/237.1, 237.2, 356/237.3, 237.4, 237.5, 239.1, 239.2, 239.7, 239.8

(56) References Cited

U.S. PATENT DOCUMENTS

| | | | | |
|---|---|---|---|---|
| 4,082,458 A | * | 4/1978 | Fukui et al. ................. | 356/432 |
| 4,377,238 A | * | 3/1983 | Wilks et al. ................. | 209/564 |
| 5,030,008 A | * | 7/1991 | Scott et al. .................. | 348/126 |
| 5,386,293 A | * | 1/1995 | Barnard et al. .............. | 348/125 |
| 5,479,252 A | * | 12/1995 | Worster et al. ......... | 250/559.42 |
| 5,583,632 A | * | 12/1996 | Haga ........................... | 356/129 |
| 5,745,236 A | * | 4/1998 | Haga ........................... | 356/371 |
| 6,069,690 A | * | 5/2000 | Xu et al. .................. | 356/237.3 |
| 6,310,689 B1 | * | 10/2001 | Ishikawa et al. ............ | 356/446 |
| 6,407,809 B1 | * | 6/2002 | Finarov et al. .......... | 356/237.3 |
| 6,414,752 B1 | * | 7/2002 | Sullivan et al. .......... | 356/237.2 |
| 2002/0015148 A1 | * | 2/2002 | Tomomatsu .............. | 356/237.2 |

FOREIGN PATENT DOCUMENTS

| | | |
|---|---|---|
| JP | 61-149807 U | 9/1986 |
| JP | 62-103548 A | 5/1987 |
| JP | 09-139162 A | 5/1997 |
| JP | 2000-055826 A | 2/2000 |

* cited by examiner

*Primary Examiner*—Michael P. Stafira
*Assistant Examiner*—Juan D Valentin, II
(74) *Attorney, Agent, or Firm*—Banner & Witcoff, Ltd.

(57) ABSTRACT

The unit for inspecting a surface is to detect a flaw on a specular surface of an object to be inspected with accuracy. The unit is so arranged that light 1*a* is irradiated from a point light source or close to a point light source 4, the light 1*a* is refracted by a Fresnel lens 5 so as to converge in a condition of being close to parallel, the refracted light 1*a* is reflected by a half mirror 6, the light 1*a* is irradiated on generally whole area of the specular surface 2 to be inspected and the reflected light 1*a* is introduced into an image capturing means 10 provided at a position where the light 1*a* converges.

19 Claims, 22 Drawing Sheets

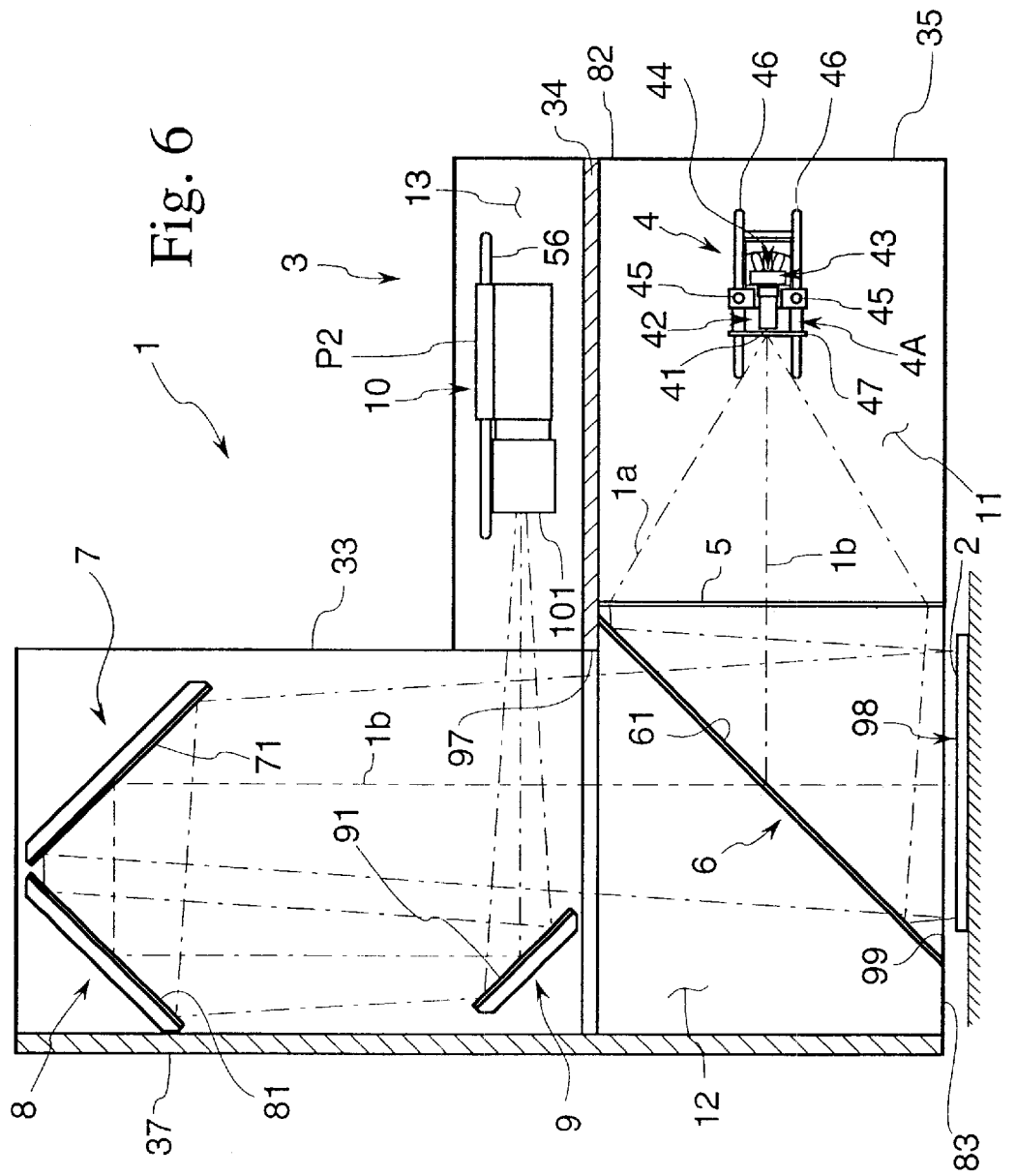

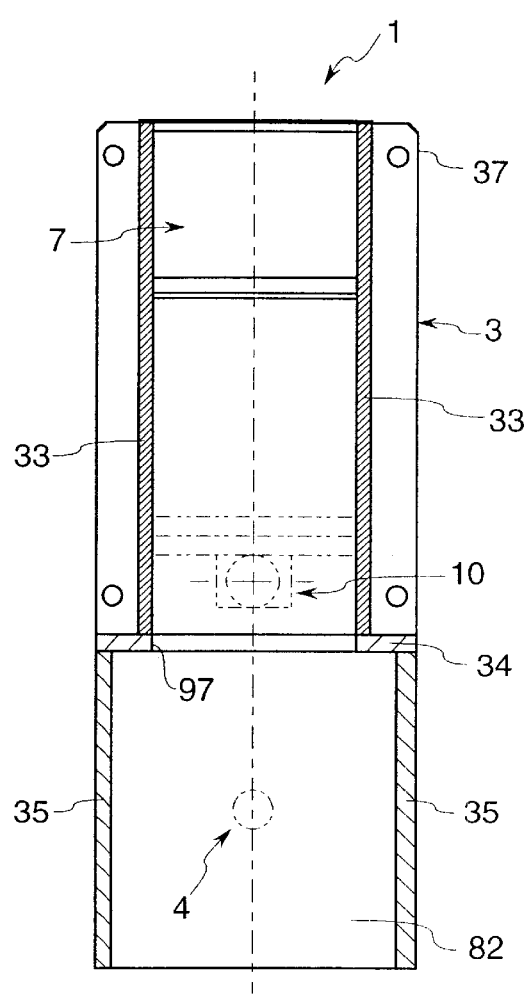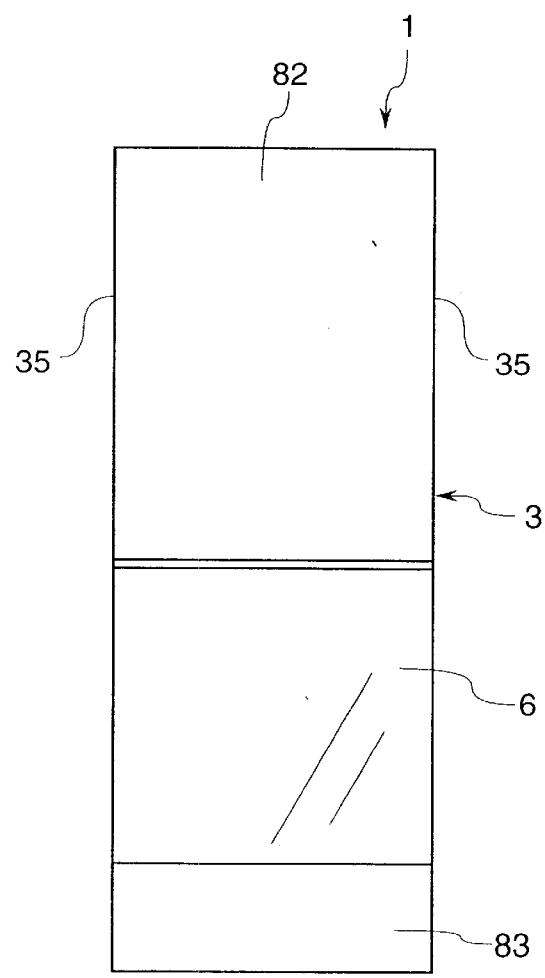

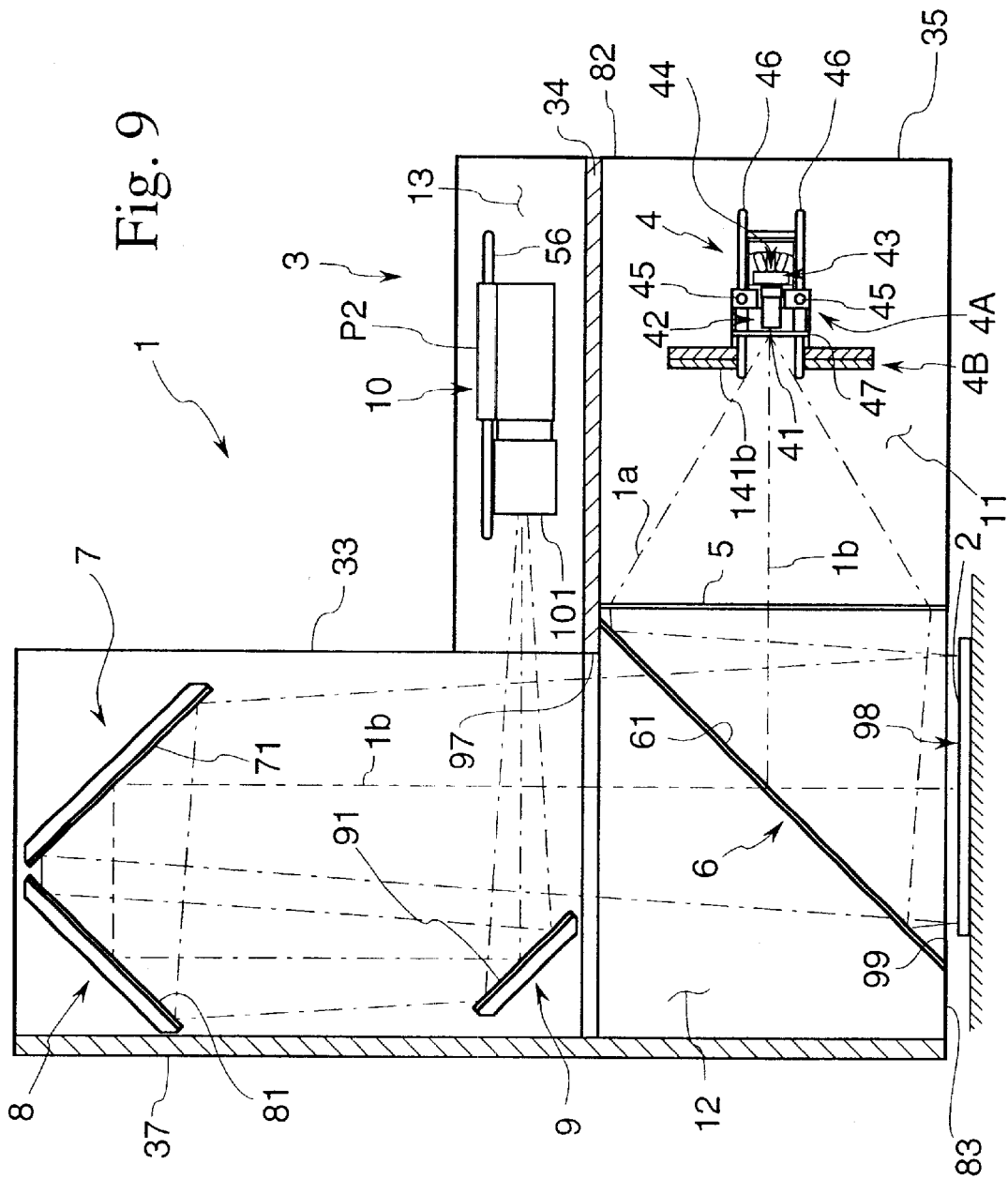

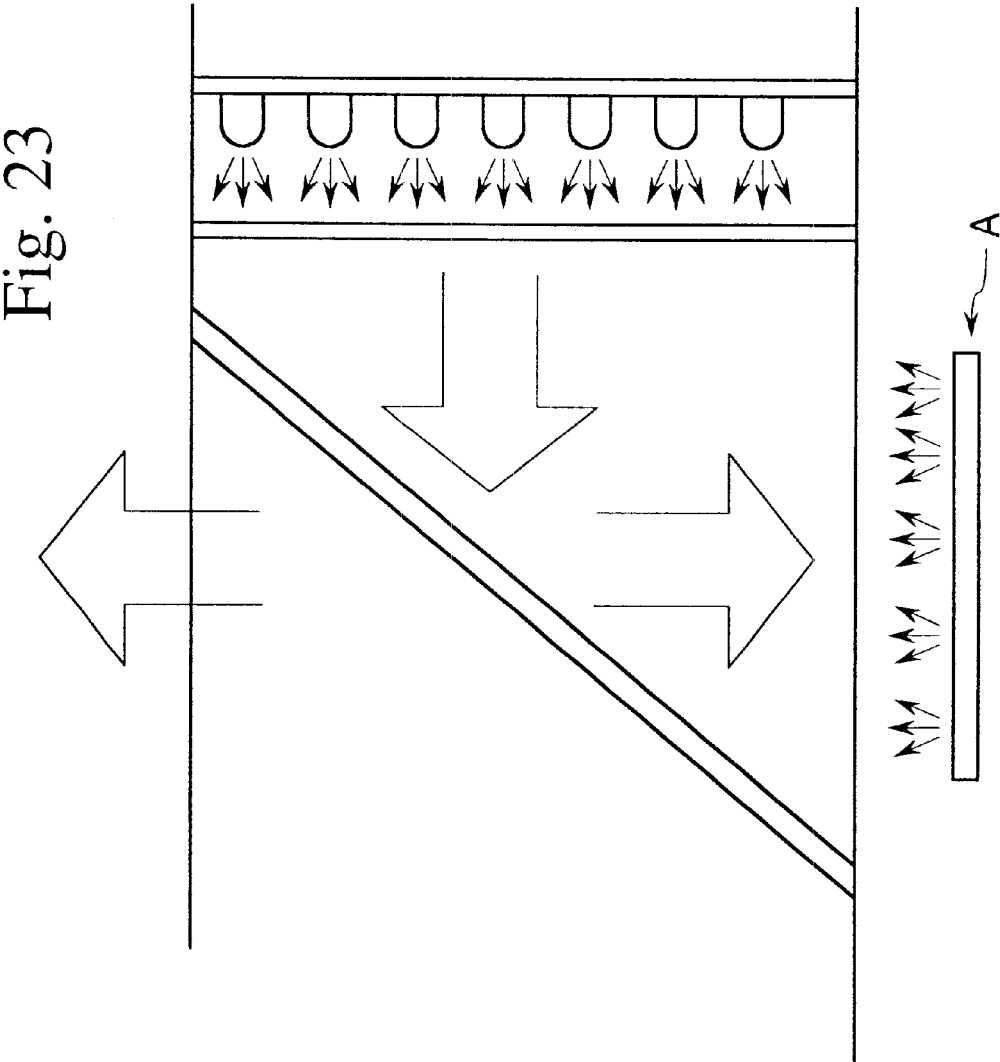

UNIT FOR INSPECTING A SURFACE

BACKGROUND OF THE INVENTION AND RELATED ART STATEMENT

This invention relates to a unit for inspecting a surface which is for inspecting mainly a flaw made on an object to be inspected which has a specular surface such as a CD, a semiconductor wafer, a DVD, an MD or the like.

Conventionally, a variety of units for inspecting a surface are devised in order to inspect a flaw made on an object to be inspected which has a specular surface such as a CD, a semiconductor wafer or the like. As one of the units for inspecting a surface, the unit shown in FIG. 23 is already known in which light from a lighting unit having an area illuminant is irradiated uniformly on a surface of an object to be inspected so as to detect whether there is a flaw or rot by capturing an image of the reflected light.

However, in case a surface to be inspected is specular, if light which is not parallel such as diffused light irradiated from a plurality of light sources is irradiated on the surface, a flaw or a carved mark on the surface might not be detected, thereby to hinder an effective inspection on the surface. More concretely, as shown in FIG. 21, if a flaw is subtle such as a scratching linear flaw 92 or a point flaw 92, it is extremely difficult to detect the flaw.

OBJECT AND SUMMARY OF THE INVENTION

In order to solve the above problems, a unit for inspecting a surface in accordance with this invention is so arranged that light irradiated from a point light source or close to a point light source is refracted by a lens so as to gradually converge in a condition of being close to parallel, the light is irradiated on a surface to be inspected and an image capturing means is arranged at a position where the reflected light converges.

More particularly, a unit for inspecting a surface is utilized in inspecting a flaw generated on a specular surface to be inspected or in reading a carved mark on a specular surface to be inspected and is characterized by that an illuminating means having a point illuminating element as a point light source or close to a point light source, a Fresnel lens, a half mirror and an image capturing means are supported by a body, wherein light is irradiated from the illuminating means, the light is refracted by the Fresnel lens so as to converge in a condition of being close to parallel, the refracted light is reflected by the half mirror, the light is irradiated on the specular surface to be inspected, the refracted light by the Fresnel lens is reflected against the half mirror, the reflected light is irradiated on generally whole area of the surface to be inspected and the reflected light is introduced into the image capturing means provided at a position where the light converges.

In accordance with the arrangement, clear light and shade contrast is shown between the portion where a flaw is formed and the other portion. This makes it possible to detect a subtle flaw such as a linear flaw or a point flaw which has not been able to be detected with conventional units for inspecting a surface. It is considered that this phenomenon is caused due to the following reasons.

When light having a converging characteristics is irradiated on a specular surface of an object to be inspected, a reflected image is introduced into an image capturing means in a condition that the image is gradually reduced as the light converges while the light irradiated on a portion where a flaw is formed reflects in a direction different from a converging direction due to subtle concave and convex of the flaw. As a result, it is considered that the light reflected from the portion where the flaw is formed does not reach the image capturing means, which makes the portion appear to be dark on the image captured by the image capturing means.

For an object whose surface to be inspected is relatively large such as a CD, a semiconductor wafer, a DVD or an MD, a length of an optical path is required to be lengthened quite a lot in order to make almost parallel light convergent, therefore it is difficult to make a size of the unit for inspecting a surface realistic. In order to effectively solve this problem, it is preferable that light reflected against a surface to be inspected is introduced into an image capturing means by reflecting the light a plurality of times against a plurality of reflecting mirrors provided inside a body of a unit. In addition, a thin, short in focal length and low-priced Fresnel lens makes a contribution on downsizing the unit and a low price.

For making an image captured by the image capturing means not to be upside down or not to be contrary in right and left to the actual object, it is preferable that an even number of the reflecting mirrors are provided.

In order to make it easy to adjust a position where an image is created or to adjust field of the image capturing means so as to deal with a change of an optical path length due to a difference of a position where an object to be inspected is placed, it is preferable that the image capturing means can be detachably mounted on outside the body of the unit, a refracting lens is arranged both on an optical axis of the light and near the image capturing means, and the refracting lens can be moved slidably along the optical axis, that the illuminating means is arranged to move along an optical axis of the light irradiated from the illuminating means, or that the image capturing means is arranged to move along the optical axis of the light introduced into the image capturing means.

As a concrete example of the embodiment, it is represented that the point illuminating element comprises a column-shaped optical Transmitting body having a light guiding face at one end thereof and an illuminating face at the other end thereof and a plurality of LEDs or photo fibers arranged so as to gather the irradiated light on the light guiding face of the column-shaped optical transmitting body, and is so arranged that the light is irradiated from the illuminating face wherein a light diffusing portion is provided on the illuminating face of the column-shaped optical transmitting body so that light diffusion effect is produced.

In order to inspect a surface satisfactorily it is preferable that a part or whole of the body is provided with a delustered processing.

Further, in order to make it possible to inspect not only a specular surface but also, for example, if a CD, a back of the specular surface such as a printed surface so as to improve general purpose properties of the unit, it is preferable that light is irradiated from an illuminating means provided near a focal point of a Fresnel lens, the light is refracted by the Fresnel lens so as to converge, the refracted light is reflected against a half mirror, the light is irradiated on generally whole area of a specular surface to be inspected and the reflected light is introduced into an image capturing means wherein the illuminating means comprises a point illuminating element as a point light source or close to a point light source and a ring-shaped area illuminating element arranged to surround the point illuminating element, and the point illuminating element and the area illuminating element are so arranged to be switched to illuminate.

More specifically, the point illuminating element is illuminated for inspecting a specular surface as mentioned above while the area illuminating element is illuminated for inspecting a printed surface or the like.

In accordance with the arrangement, other surfaces such as a printed surface besides a specular surface can be inspected by means of the area illuminating element. Especially with the unit, the light irradiated from the illuminating element is promoted to diffuse by passing through the Fresnel lens, thereby to improve accuracy of inspection. In this case, it is preferable that the light irradiated from the illuminating element is white and the image capturing unit can display in color.

As a concrete example of the area illuminating element, it is represented that comprising a disk-shaped transparent body, a disk-shaped supporting plate which is overlapped with one of the face plates of the transparent body and a plurality of LEDs arranged to surround the transparent body so as to illuminate light toward the center of the transparent body and provided with a through hole at the center thereof to pass through the light irradiated from the point illuminating element wherein the other face plate of the transparent body is made to area-illuminate the light as an illuminating face.

In accordance with the above-mentioned invention, clear light and shade contrast is shown between the portion where the flaw is formed and the other portion. This makes it possible to detect a linear flaw such as a scratch or a subtle flaw due to a bump trace which has not been able to be detected with conventional units for inspecting a surface and to read a carved mark.

In case this method is simply used, in order to deal with an object whose surface to be inspected is relatively large such as a CD or a DVD, a unit for inspecting a surface is likely to be large-sized and high-priced as mentioned above. However, if a lens used for making light parallel is a thin, short in focal length and low-priced Fresnel lens and light reflected against a surface to be inspected is introduced into an image capturing means by reflecting the light a plurality of times against a plurality of reflecting mirrors provided inside the unit, it is possible to realize a reasonable size and price for actual use.

If a number of a reflecting mirror provided is an even number, an image taken by the image capturing means can be made not to be upside down to the actual object or not to be contrary in right and left direction to the actual object.

If the image capturing means is detachably mounted in position on outside the body, a refracting lens is arranged on an optical axis of the light and near the image capturing means, and the refracting lens can be moved slidably along the optical axis, the illuminating means is provided to slidably move along an optical axis of the light irradiated from the illuminating means or the image capturing means is provided to slidably move along the optical axis of the light introduced from the illuminating means, it becomes possible to adjust a position where an image is created or to adjust view in flexibly cooperation with a change of an optical length due to difference of a position where an object to be inspected is set.

If the illuminating element comprises a column-shaped optical transmitting body having a light guiding face at one end thereof and an illuminating face at the other end thereof and a plurality of LEDs or photo fibers arranged so as to gather the irradiated light on the light guiding face of the column-shaped optical transmitting body, and is so arranged that the light is irradiated from the illuminating face and a light diffusing portion is provided on the illuminating face of the column-shaped optical transmitting body so that light diffusion effect is produced, part of the light irradiated on a portion where no flaw is made reflects so as not to converge because of a mounting error or distortion of the Fresnel lens or a subtle inclination or warp of the plate where a CD or DVD is placed. As a result, a portion where no flaw is made in an image shown on the image capturing means becomes a little dark, thereby to avoid a case that contrast between the portion where a flaw is made and other portion is blurred. This makes it possible to allow a mounting error or distortion of the Fresnel lens or a subtle inclination or warp of the plate where the object to be inspected is placed to a certain degree.

If a part or whole of the body of the unit is provided with a delustered processing, it is possible to conduct surface inspection satisfactorily.

If the illuminating means comprises a point illuminating element as a point light source or close to a point light source and a ring-shaped area illuminating element arranged to surround the point illuminating element and the point illuminating element and the area illuminating element are so arranged to be switched to illuminate, the point illuminating element can be illuminated for inspecting a specular surface as mentioned above while the area illuminating element can be illuminated for inspecting a printed surface or the like. As a result, other surfaces such as a printed surface besides a specular surface can also be inspected, thereby to improve general purpose properties of the unit. Especially with the unit, the light irradiated from the illuminating element is promoted to diffuse by passing through the Fresnel lens, thereby to improve accuracy of inspection.

If the area illuminating means comprises a disk-shaped transparent body, a disk-shaped supporting plate which is overlapped with one of the face plates of the transparent body and a plurality of LEDs arranged to surround the transparent body so as to illuminate light toward the center of the transparent body and is so arranged that a through hole is provided at the center thereof to pass through the light irradiated from the point illuminating element and the other face plate of the transparent body is made to area-illuminate the light as an illuminating face, it is possible to realize a preferable unit for inspecting a surface by making use of an LED's characteristic of long life.

BRIEF DESCRIPTION OF THE DRAWINGS

FIG. 6 is a cross-sectional side view showing an internal structure of the unit for inspecting a surface in accordance with the embodiment.

FIG. 7 is a front view showing the unit for inspecting a surface in accordance with the embodiment.

FIG. 8 is a bottom view showing the unit for inspecting a surface in accordance with the embodiment.

FIG. 9 is a cross-sectional side view showing an internal structure of a unit for inspecting a surface in accordance with the third embodiment.

FIG. 23 is a schematic diagram showing a conventional unit for inspecting a surface.

DETAILED DESCRIPTION OF THE PREFERRED EMBODIMENTS (The First Embodiment)

The first embodiment of the invention will be described in detail with reference to FIGS. 1 through 4.

Figure 1:
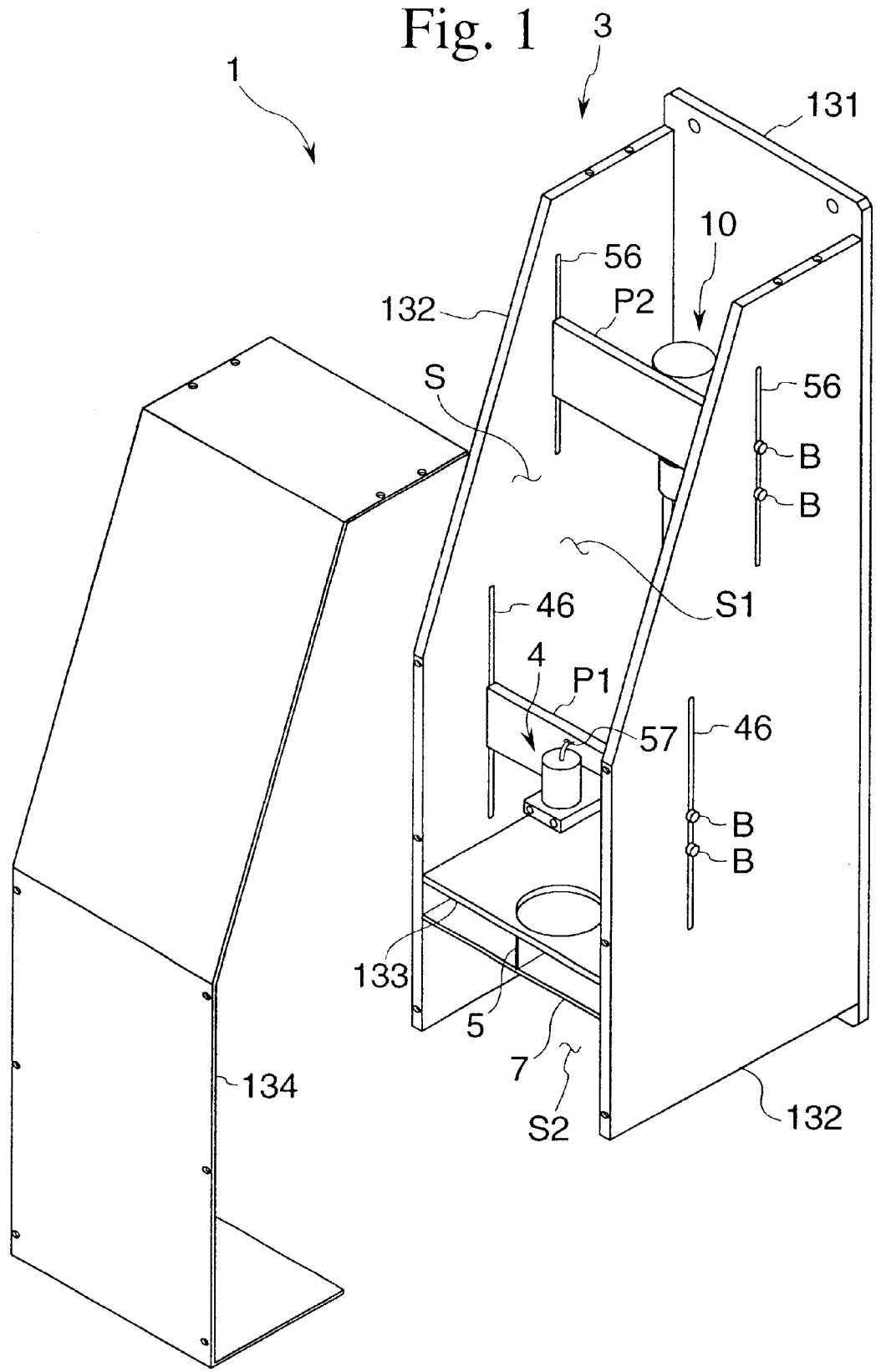
FIG. 1 is an explosive perspective view showing a unit for inspecting a surface in accordance with the first embodiment of the present claimed invention.
Figure 2:
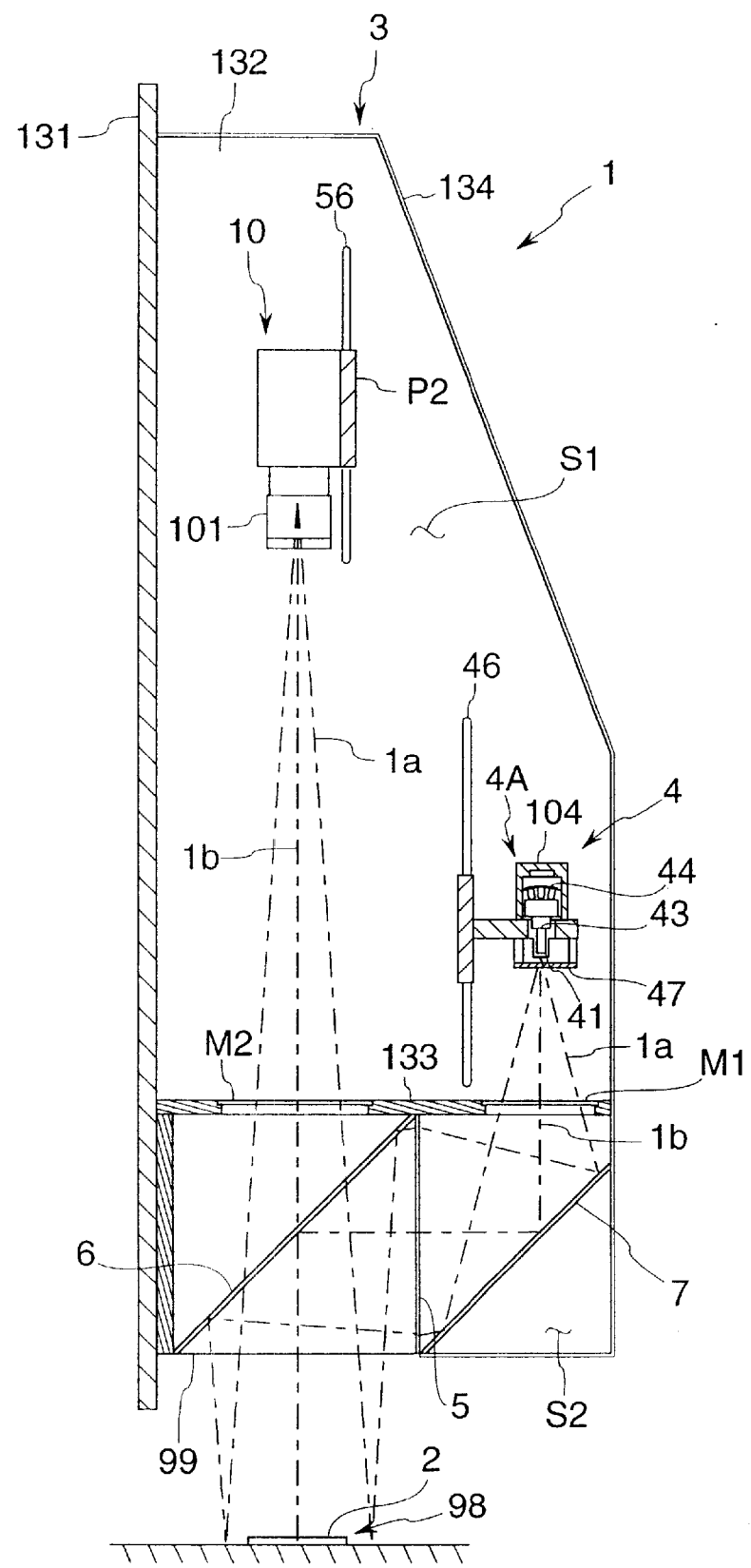
FIG. 2 is a cross-sectional side view showing an internal structure of the unit for inspecting a surface in accordance with the embodiment.
Figure 3:
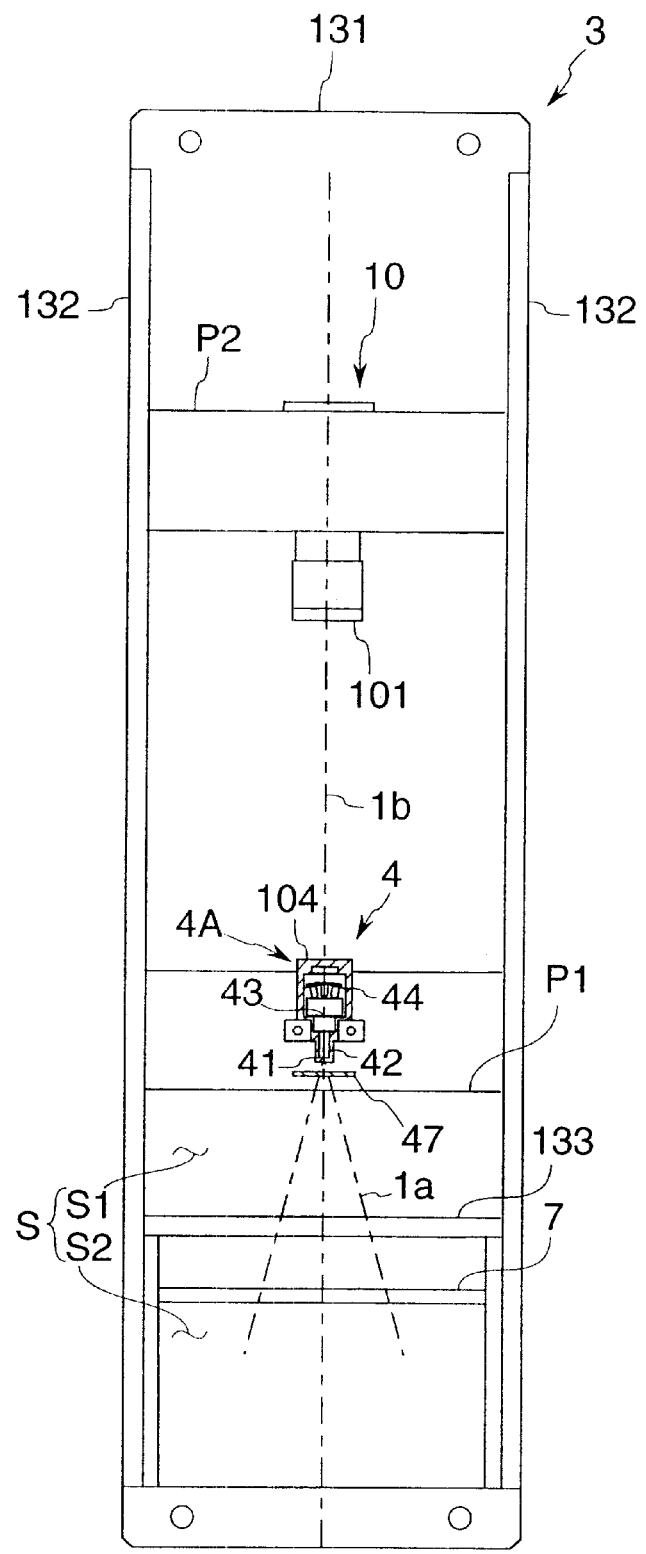
FIG. 3 is a front view showing the unit for inspecting a surface in accordance with the embodiment.

A unit 1 for inspecting a surface shown in FIGS. 1 through 3 is, for example, to inspect a flaw 92 made on a specular portion 2 as a surface to be inspected of an object 98 under inspection such as a CD, a DVD or the like. The unit 1 for inspecting a surface comprises a casing 3 as a body, an illuminating means 4 a total reflecting mirror 7, a Fresnel lens 5, a half mirror 6 and a CCD camera 10 as an image capturing means.

More specifically, the casing 3 comprises a rectangular front plate 131 whose long side is erected vertically, a pair of side plates 132 extending from the long sides of the front plate 131 rearward, and the side plates 132, a dividing plate 133 bridged between the side plates 132 so as to divide an internal space S formed by the front plate 131 vertically into a first space S1 and a second space S2 and a cover 134 which covers the side plates 132 to surround sides of the side plates 132 from outside. General half part facing the front plate 131 of a bottom end between the side plates 132 is so made not to be covered by the cover 134 and an opening 99 is formed at the part. Each of the above-mentioned components is provided with a black anodized aluminum processing as a delustered processing.

The illuminating means 4 is made of a column-shaped optical transmitting body 42 having a light guiding face 43 at a front end thereof and an illuminating face 41 at a base end thereof, and a point light source element 4A comprising a plurality of LEDs 44 arranged so as to gather the irradiated light on the light guiding face 43 of the column-shaped optical transmitting body 42, both of which are incorporated in a stepped cylinder-shaped box body 104 and so arranged that light 1a is irradiated from the illuminating face 41. in this embodiment, it is so arranged that light diffusion effect is produced at an overlapped portion by overlapping a plate-shaped light diffusing panel 47 with the illuminating face 41 of the column-shaped optical transmitting body 42.

The illuminating means 4 is supported by the side plates 132 through a plate P1 for supporting an illuminating means in a posture that the illuminating face 41 faces downward on a side of anti-front plate in the first space S1, namely in a posture that the light 1a is irradiated downward along the vertical direction. The plate P1 for supporting an illuminating means is arranged between the side plates 132 to allow slidable movement along a vertical direction, more concretely, a screw B is passed through a through groove 46 extending vertically and provided on he side plates 132 and the screw B is tightened to or loosened from a threaded hole, not shown in drawings, provided or the side edges of the plate Pl for supporting an illuminating means so as to move the plate P1 and the illuminating means 4 along an optical axis 1b or so as to fix them.

The total reflecting mirror 7 is a plane mirror fixed at an angle of 45 degrees on a side of anti-front plate in the second space S2. The total reflecting mirror 7 changes a direction of the light traveling downward along the vertical direction which is irradiated from the illuminating means 4 at 90 degrees so as to make the light 1a travel horizontally toward the front plate 131.

The Fresnel lens 5 is arranged to erect vertically in parallel with the front plate 131 at a position so that the optical axis 1b of the light 1a reflected by the total reflecting mirror 7 passes the center of the Fresnel lens 5 and the light 1a which has passed through the Fresnel lend 5 is refracted so as to converge in a condition of being close to parallel. The Fresnel lens 5 is larger in diameter than that of the largest object which can be inspected (100 mm in this embodiment).

The half mirror 6 is a plane mirror which reflects generally half of the irradiated light 1a and through which the remaining half thereof permeates. The half mirror 6 is fixed above the opening 99 in front of the Fresnel lens 5 on the side of the front plate in the second space S2 in a posture in parallel with the total reflecting mirror 7, namely at an angle of 45 degrees.

The CCD camera 10 is supported by the side plates 132 through a plate P2 for supporting a camera vertically above the half mirror 6 in the first space S1 in a posture that a lens of the CCD camera 10 faces downward along the vertical direction, namely in a posture that the light 1a traveling from downward along the vertical direction can be introduced thereinto. The plate P2 for supporting a camera is arranged between the side plates 132 to allow slidable movement along a vertical direction, more concretely, a screw B is passed through a through groove 56 extending vertically and provided on the side plates 132 and the screw B is tightened to or loosened from a threaded hole, not shown in drawings, provided on the side edges of the plate P2 for supporting a camera so as to move the plate P2 and the CCD camera 10 along the optical axis 1b or so as to fix them. The CCD camera 10 is provided with a cord 57 through which a captured image or the like can be output and a connector, which is not shown in drawings, provided at a front end of the cord 57 so as to see the image on a display or the like.

An operation of the above-explained unit 1 for inspecting a surface will be explained.

First, the object 98 to be inspected such as a CD, an MD or the like is arranged outside of the casing 3 in a posture that a specular portion 2 of the object 98 faces the opening 99.

Subsequently, the illuminating means 4 is operated. Then the light 1a irradiated from the illuminating means 4 travels downward diffusely along the vertical direction and passes through a first through window M1 provided on the dividing plate 133, followed by changing a direction of traveling to forward horizontally due to being reflected by the total reflecting mirror 7.

Then the light 1a is refracted to gradually converge by passing through the Fresnel lens 5. The refracted light 1a is reflected by the half mirror 6, and a part of the refracted light 1a changes a direction of traveling downward along the vertical direction and passes through the opening 99 to be irradiated on the specular portion 2 of the object 98 to be inspected placed outside of the casing 3.

The light 1a irradiated on the specular portion 2 is reflected against the specular portion 2 and travels upward along a vertical direction, passes through the opening 99, the half mirror 6 and a second through window M2 provided the dividing plate 133, gradually converges so as to be captured by the CCD camera 10 in a condition of being close to convergence.

Figure 4:
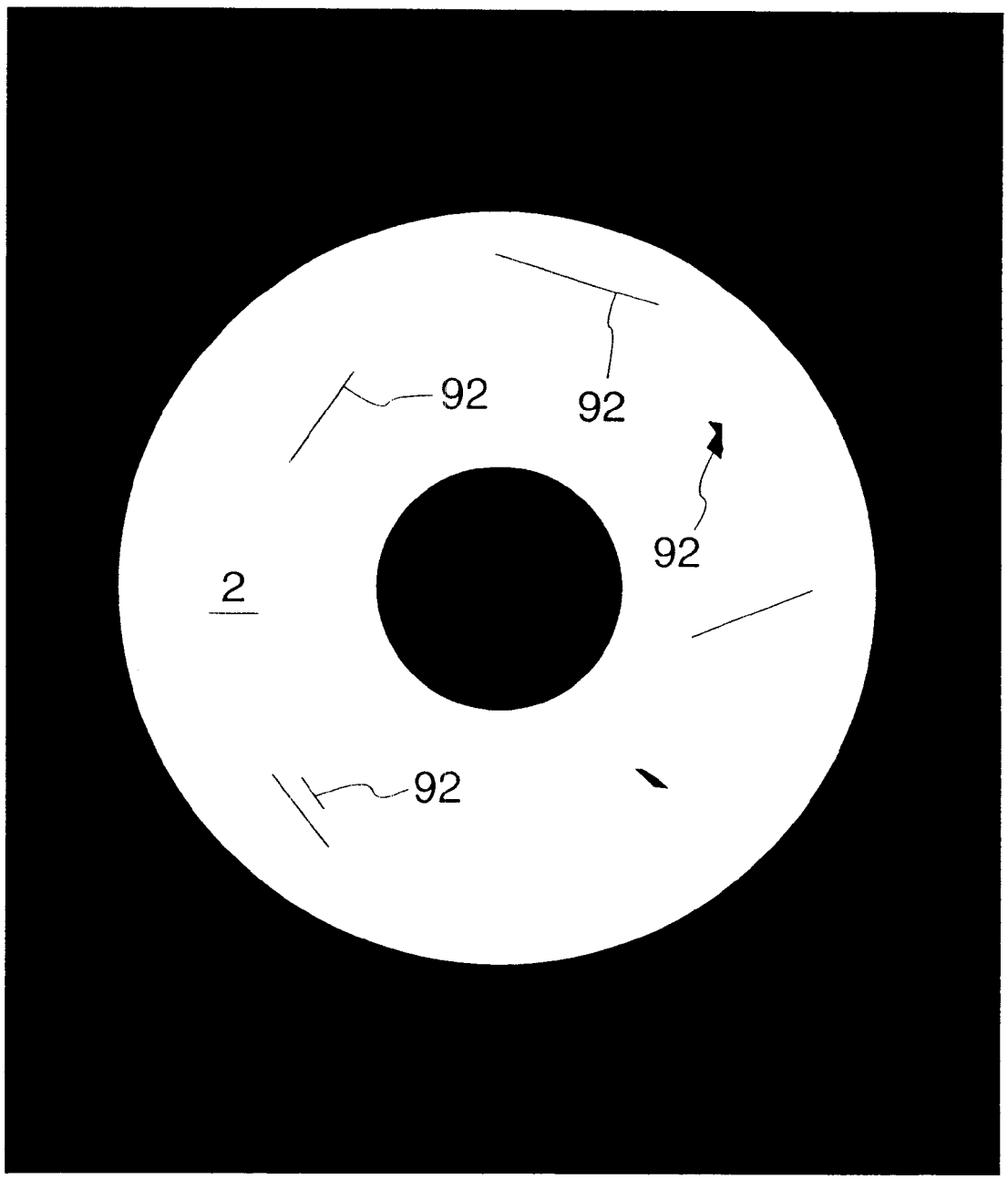
FIG. 4 is an image of a CD taken by a CCD camera in accordance with the embodiment.
Figure 5:
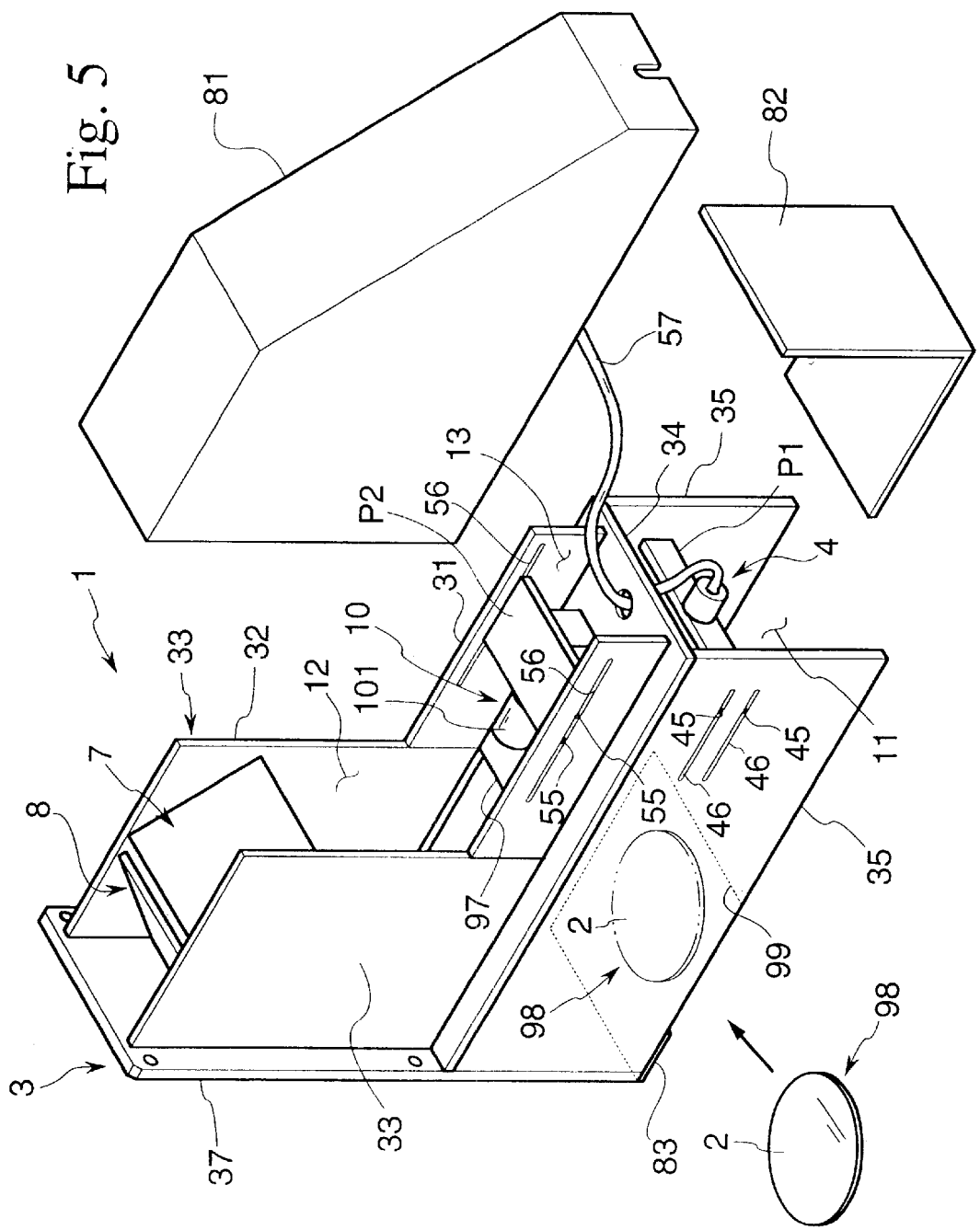
FIG. 5 is an explosive perspective view showing a unit for inspecting a surface in accordance with the second embodiment of the present claimed invention.
Figure 10:
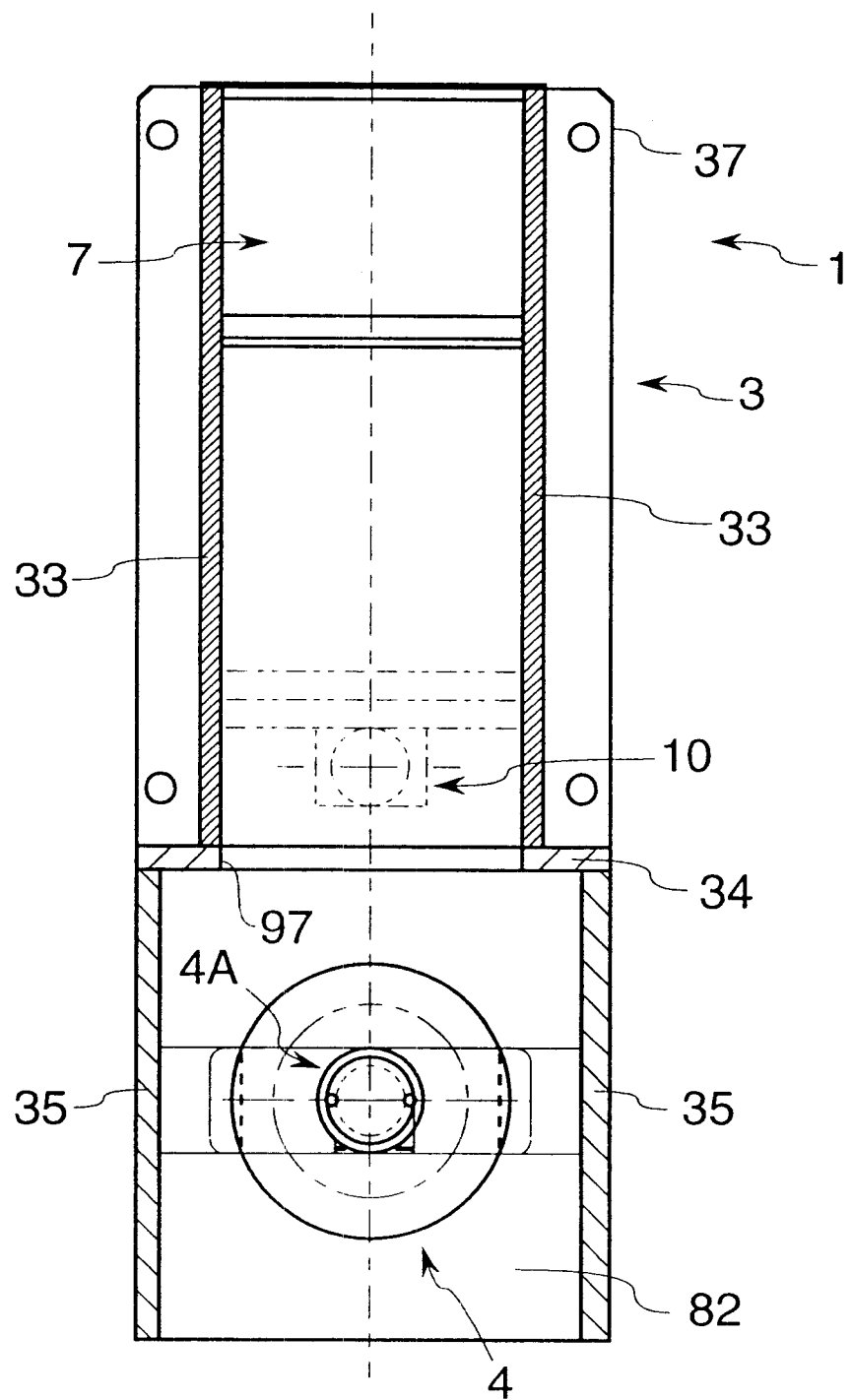
FIG. 10 is a front view showing the unit for inspecting a surface in accordance with the embodiment.

In accordance with the arrangement, since the light la irradiated on a portion where the flaw 92 is formed reflects in a direction which is different from a direction of converging due to a subtle concave or convex of the flaw 92, a reflected image is captured in a condition lack of the light 1a which reflects from the portion where the flaw 92 is formed. As a result, a clear light and shade contrast is shown between the portion where the flaw 92 is formed and the other portion, as shown in FIG. 4. This makes it possible to detect a linear flaw 92 such as a scratch or a subtle flaw 92 due to a bump trace which has not been able to be detected with conventional units for inspecting a surface. In addition, not only flaws but also carved marks can be read clearly, thereby to be able to apply the unit 1 for inspecting a surface to a unit for reading carved marks.

Further, since the Fresnel lens 5 is thin, short in focal length and low in price, it can preferably deal with an object having a relatively big specular portion 2 such as a CD or a DVD.

In order to improve the above-described accuracy of detection, theoretically it is preferable to make the illuminating means 4 close to a point light source as much as possible and to make the refracted light 1a to be parallel as much as possible. If the light 1a is made to be too much close to the theory, however, the light 1a can not be captured because of a mounting error or distortion of the Fresnel lens 5 or a subtle inclination or warp of a plate where a CD or DVD is placed, resulting in a case that a portion where no flaw is formed might also be shown black in an image on the CCD camera 10.

Then in this embodiment, the light 1a irradiated from the light illuminating means 4 is diffused by the light diffusing panel 47, which makes an illuminating area a little wider. This makes it possible to allow a mounting error or distortion of the Fresnel lens 5 or a subtle inclination or warp of the plate where an object to be inspected 98 is placed to a certain degree. As a result, the unit 1 can be made extremely preferable in practice.

In addition, since the illuminating means 4 and the CCD camera 10 are arranged to move slidably along the optical axis 1b, it is easy to adjust the illuminating means 4 and the CCD camera 10 to a position where the object 98 to be inspected is placed or a position where an image is created is swerved due to deterioration with age.

Further, since the casing 3 is provided with the delustered processing by means of a black anodized aluminum processing, it can suppress light scattering inside of the casing 3. Then the above-mentioned effects can be made conspicuous, thereby to improve reliability of the unit 1 for inspecting a surface.

Figure 22:
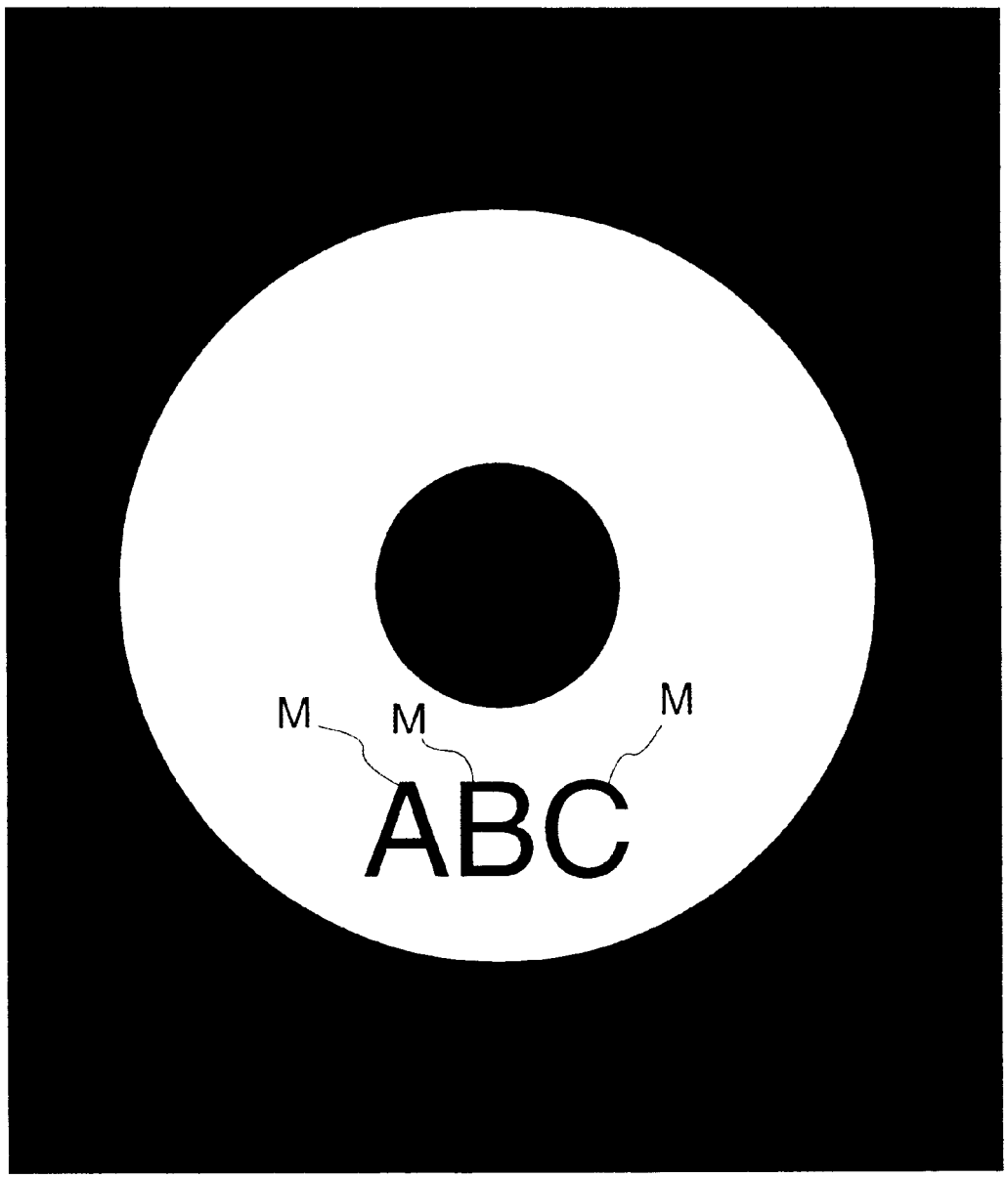
FIG. 22 is an image of a surface having a printed character taken by a CCD camera of the unit for inspecting a surface in accordance with the first embodiment of the invention.

In addition, with the above-mentioned unit 1 for inspecting a surface, it is possible to distinguish a printed character M provided on a specular portion of the CD. The reason is that the light irradiated on the surface to be inspected reflects diffusely against the printed character M, while the light reflects against the specular portion where no printed character M is provided in a convergent state. Then clear light and shade contrast is shown between a part where the printed character M is provided and other part, as shown in FIG. 22. This makes it possible to show contrast of printing state clearly on the image capturing means such as a CCD camera or the like.

(The Second Embodiment)

A second embodiment of the present claimed invention will now be explained with referring to FIGS. 5 through 8. The same reference number is given to the element corresponding to the first embodiment.

The unit 1 for inspecting a surface shown in FIGS. 5 through 8 has the same object as that of the first embodiment and comprises a casing 3, an illuminating means 4 arranged inside the casing 3, a Fresnel lens 5, a half mirror 6, three total reflecting mirrors 7, 8 and 9 and a CCD camera 10 as an image capturing means.

The casing 3 comprises a pair of upper side plates 33 having a shape of a general L character, a level plate 34 arranged between lower edges of the upper side plates 33, lower side plates 35 each of which hangs from right and left ends of the level plate 34, a rear plate 37 arranged along rear edges of the upper side plates 33 and the lower side plates 35, an upper cover 81 which covers the upper side plates 33 from upward, a lower cover 82 whose side view is an L character and which is arranged along a front half part of the lower edge and a front edge of the lower side plates 35 and and a bottom cover 83 arranged between rear ends of the bottom edges of the lower side plates 35. The casing 3 is also provided with an opening 99 to see an object 98 to be inspected at a rear half bottom thereof and an opening 97 at a rear half of the level plate 34 so as to locate above the opening 99. A room 11 for placing an illuminating means, a room 12 for placing a mirror and a room 13 for placing an image capturing means are formed inside of the casing 3. Each of the above-mentioned components is provided with a black anodized aluminum processing as a delustered processing.

The room 11 for placing an illuminating means is formed in a lower front half portion of the casing 3 and surrounded by the level plate 34, the lower side plates 35 and the lower cover 82. Inside the room 11 contained is the illuminating means 4.

The room 12 for placing a mirror is formed in a rear half portion of the casing 3 so as to locate rear of the room 11 for placing an illuminating means and surrounded by the lower side plates 35, the bottom cover 83, the upper side plates 33 and the rear plate 37. Inside the room 12 contained are three total reflecting mirrors 7, 8 and 9 and the half mirror 6.

The room 13 for placing an image capturing means locates above the room 11 for placing an illuminating means and surrounded by the upper side plates 33, the upper cover 81 and the level plate 34 and contains the CCD camera 10.

The illuminating means 4 comprises a column-shaped optical transmitting body 42 having a light guiding face 43 at a front end thereof and an illuminating face 41 at a base end thereof, and a point light source element 4A made of a plurality of LEDs 44 arranged so as to gather the irradiated light on the light guiding face 43 of the column-shaped optical transmitting body 42 and is so arranged that the light 1a is irradiated from the illuminating face 41. Further, a plate-shaped light diffusing panel 47 is provided on the illuminating face 41 of the column-shaped optical transmitting body 42 so that light diffusion effect is produced at the portion 47. In addition, the illuminating means 4 is arranged in a posture that an optical axis 1b of the irradiated light 1a is made to be horizontal facing toward the room 12 for placing a mirror along back and forth direction. In addition, in this embodiment, the illuminating means 4 is arranged in the room 11 for placing an illuminating means so as to allow back and forth movement slidably along the optical axis 1b. More concretely, the lower side plates 35 are provided with a through groove 46 extending horizontally, a screw B is passed through the through groove 46 and the screw B is tightened to or loosened from a threaded hole, not shown in drawings, provided on the side edges of a plate P1 for supporting an illuminating means 4. Then the plate P1 and the illuminating means 4 can be moved back and forth along the optical axis 1b so as to be fixed at a desired position by tightening or loosening the screw B.

The Fresnel lens 5 has an already known arrangement and a diameter of which is larger than the largest diameter (140 mm in this embodiment) of the object to be inspected which can be inspected in this embodiment. And the Fresnel lens 5 is arranged to erect at a border between the room 12 for placing a mirror and the room 11 for placing an illuminating means in a position separated from the illuminating means by more than a focal length thereof, the optical axis 1b of the light 1a irradiated from the illuminating means 4 passes through the center thereof and a face plate of the Fresnel lens 5 is at right angles with the optical axis 1b.

The half mirror 6 has an already known arrangement in which generally half of the irradiated light is reflected and the remaining half thereof is permeated. The half mirror 6 is arranged in rear of the Fresnel lens 5 above the opening 99. More concretely, the upper end of the half mirror 6 locates in front of the lower end thereof and a reflecting face 61 is in juxtaposed with right and left level axes.

Three total reflecting mirrors, namely, a first total reflecting mirror 7, a second total reflecting mirror 8 and a third total reflecting mirror 9 have a reflecting face whose area is smaller in this order and each of the total reflecting mirrors 7, 8 and 9 is to reflect the light 1a reflected against the object to be inspected 98 arranged under the opening 99 one after another and to introduce the light 1a into the CCD camera.

The first total reflecting mirror 7 is arranged above the half mirror 6. More concretely, the upper end of the first total reflecting mirror 7 locates in rear of the lower end thereof and a reflecting face 71 is in juxtaposed with right and left level axes.

The second total reflecting mirror 8 is arranged in rear of the first total reflecting mirror 7. More concretely, the upper end of the second total reflecting mirror 8 locates in front of the lower end thereof and a reflecting face 81 is in juxtaposed with right and left level axes.

The third total reflecting mirror 9 is arranged under the second total reflecting mirror 8. More concretely, the upper end of the third total reflecting mirror 9 locates in rear of the lower end thereof and a reflecting face 91 is in juxtaposed with right and left level axes.

The CCD camera 10 comprises a lens 101 and the lens 101 is so arranged that the center thereof falls on a horizontal axis which passes back and forth through a general center of the third total reflecting mirror 9 and a face plate of the lens 101 is at right angles with this horizontal axis. More concretely, a screw B is passed through a through groove 56 extending back and forth and provided on the upper side plates 33 and the screw B is tightened to or loosened from a threaded hole, not shown in drawings, provided on the side edges of the plate P2 for supporting a camera so as to move the plate P2 and the CCD camera 10 back and forth along the optical axis 1b or so as to fix them. The CCD camera 10 is provided with a cord 57 through which a captured image or the like can be output and a connector, which is not shown in drawings, provided at a front end of the cord 57 so as to see the image on a display or the like.

An operation of the above-described unit 1 for inspecting a surface will be explained.

First, a specular portion 2 of the object 98 to be inspected such as a CD or the like faces the opening 99. Subsequently, the illuminating means 4 is operated. Then the light 1a irradiated from the illuminating means 4 travels rearward diffusely along a horizontal direction and passes through the Fresnel lens 5. The light 1a is refracted to converge gradually. The refracted light 1a is reflected by the half mirror 6, and changes a direction of traveling downward along the vertical direction and passes through the opening 99 to be irradiated on the specular portion 2 of the object 98 to be inspected. The light 1a is reflected against the specular portion 2 and travels upward along a vertical direction, passes through the opening 99 and the half mirror 6, gradually converges and travels to the first total reflecting mirror 7. Next, the light 1a is reflected against the first total reflecting mirror 7 and changes a direction of traveling rearward along the horizontal direction and then the light 1a is reflected against the second total reflecting mirror 8 and changes a direction of traveling vertically downward. Finally, the light 1a is reflected against the third total reflecting mirror 9 and changes a direction of traveling horizontally forward as to be captured by the CCD camera 10 in a condition of being close to convergence.

In accordance with the arrangement, in addition to the effects of the first embodiment, since the light 1a reflected against the object to be inspected is reflected several times in the body so as to lengther an optical path length and introduced into the CCD camera 10, it can preferably deal with an object having a relatively big specular portion 2 such as a CD or a DVD as well as the unit can be downsized, thereby to enable a reasonable size and price for an actual use.

(The Third Embodiment)

A third embodiment of the present claimed invention will now be explained with referring to FIGS. 9 through 12. In the third embodiment, the arrangements other than that of the illuminating means 4 are essentially the same as those of the second embodiment. Therefore, the same reference number is given to the element corresponding to the first and second embodiments and no description will be given.

The illuminating means 4 is provided near a focal point of the Fresnel lens 5 and comprises a point illuminating element 4A which is a point light source or light source which is close to a point light source and a ring-shaped area illuminating element 4B arranged to surround the point illuminating element 4A wherein the point illuminating element 4A and the area illuminating element 4B are so arranged to be switched to illuminate.

The point illuminating element 4A is the same as that of the first embodiment in arrangement or position to be arranged, therefore, an explanation will be omitted.

Figure 11:
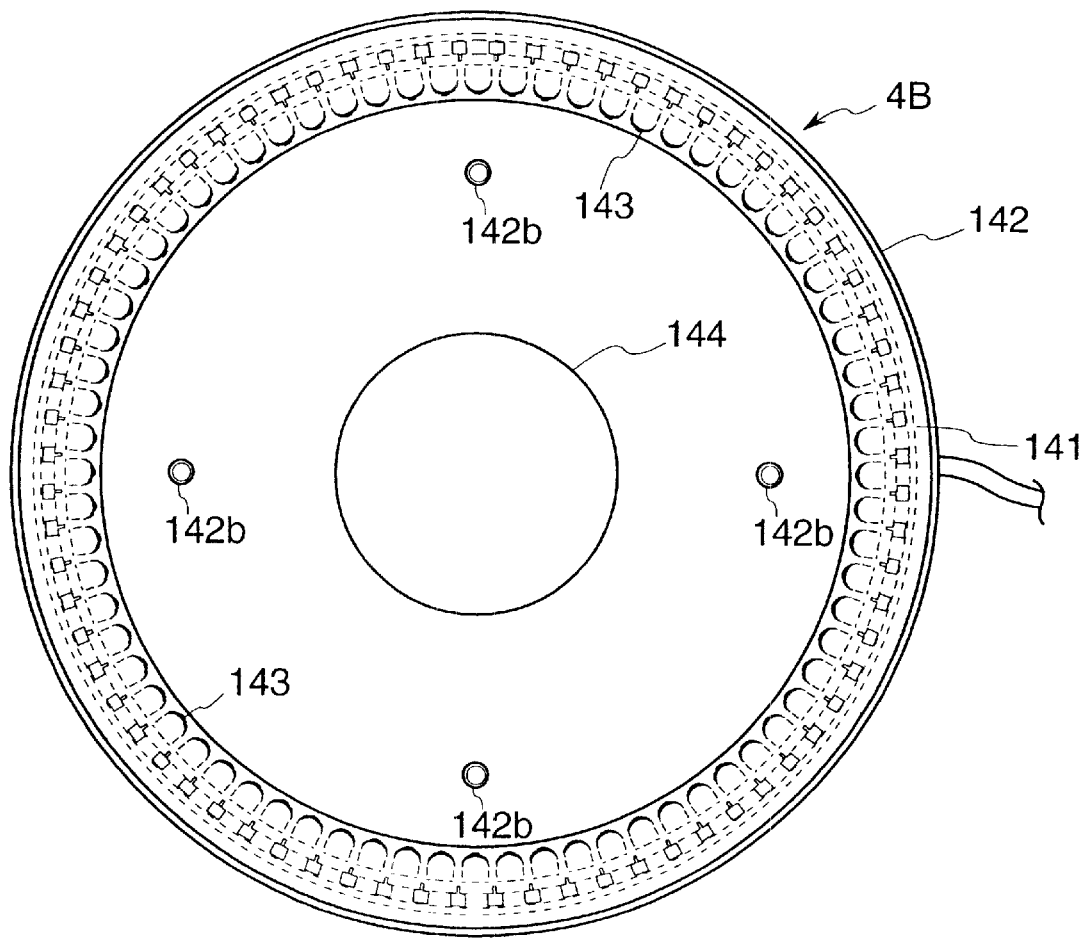
FIG. 11 is a plane view showing an area illuminating element in accordance with the embodiment.
Figure 12:
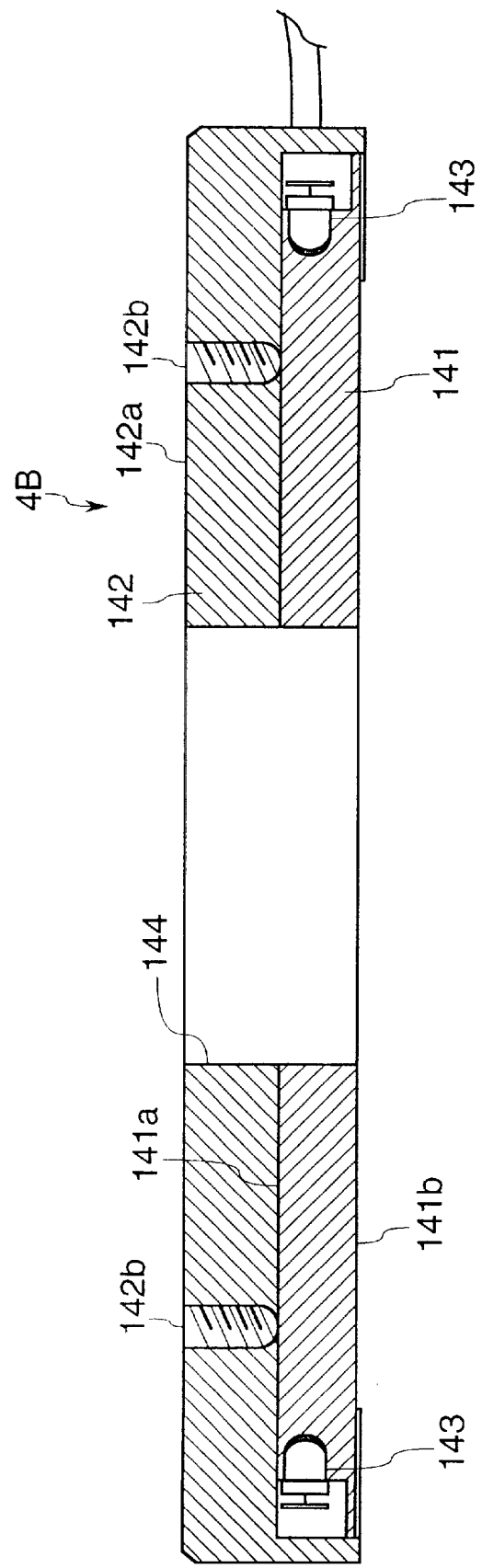
FIG. 12 is a cross-sectional view showing the area illuminating element in accordance with the embodiment.
Figure 13:
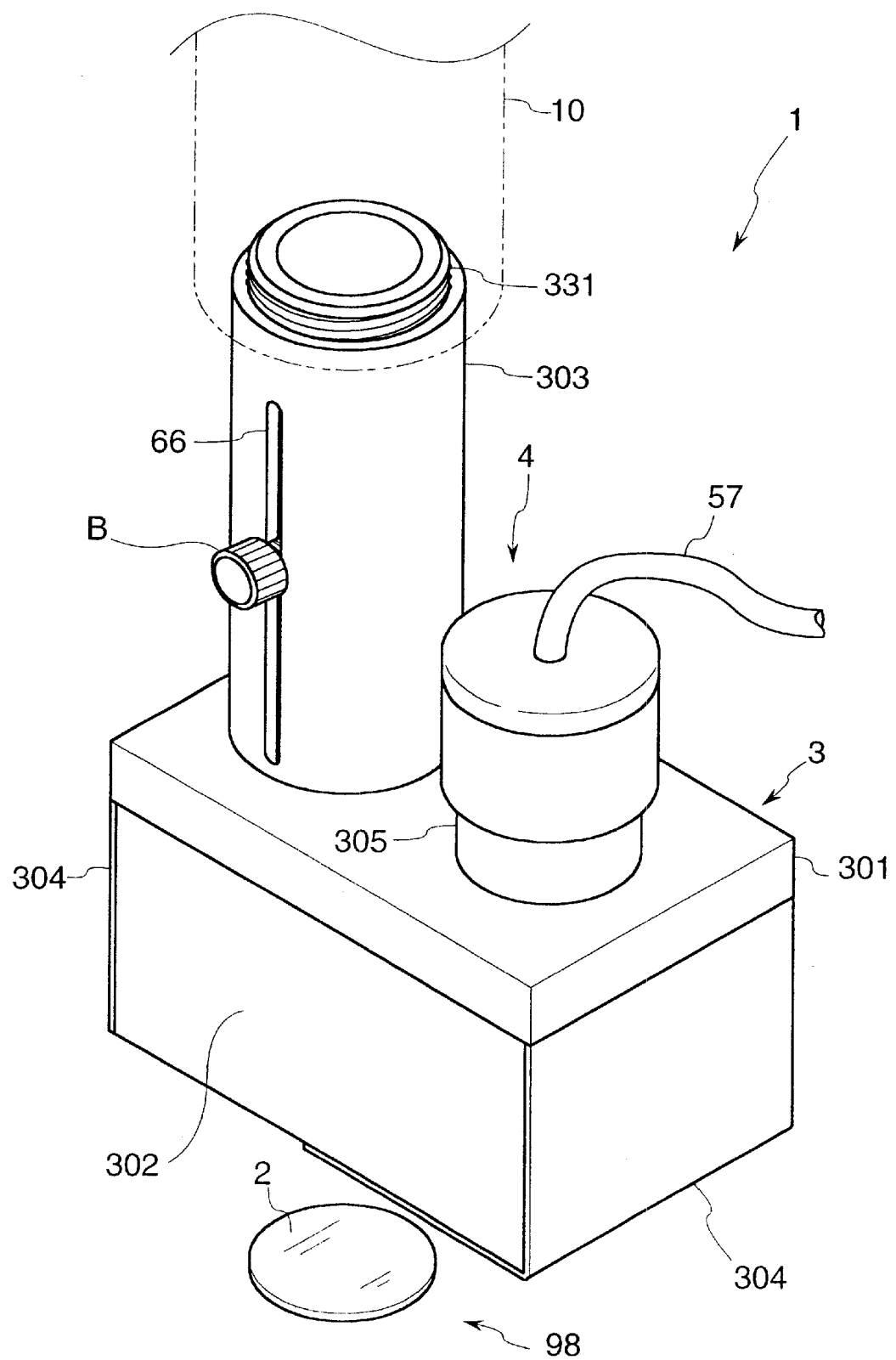
FIG. 13 is a perspective view showing a unit for inspecting a surface in accordance wish the forth embodiment of the present claimed invention
Figure 14:
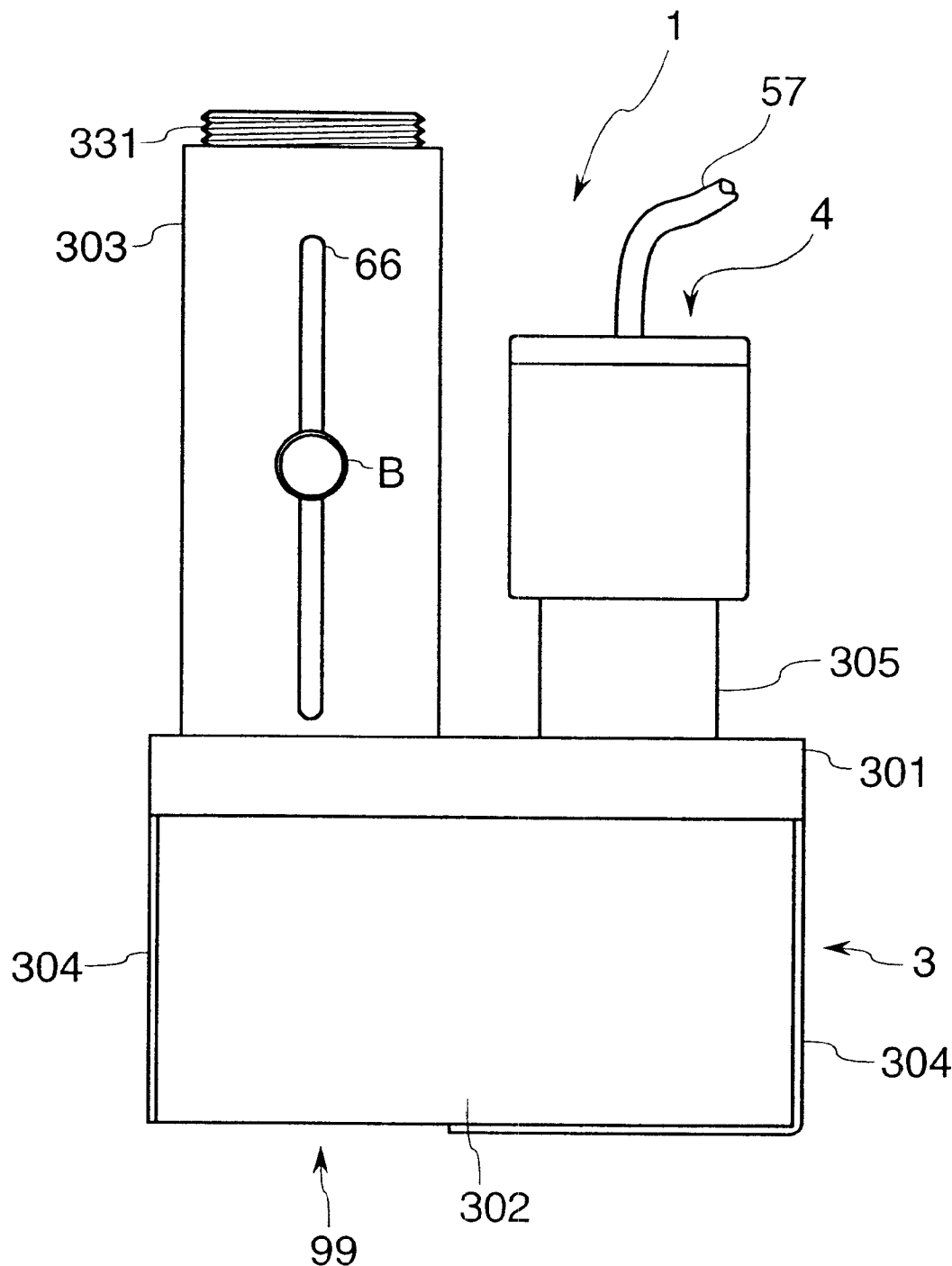
FIG. 14 is a side view of the unit for inspecting a surface in accordance with the embodiment.
Figure 15:
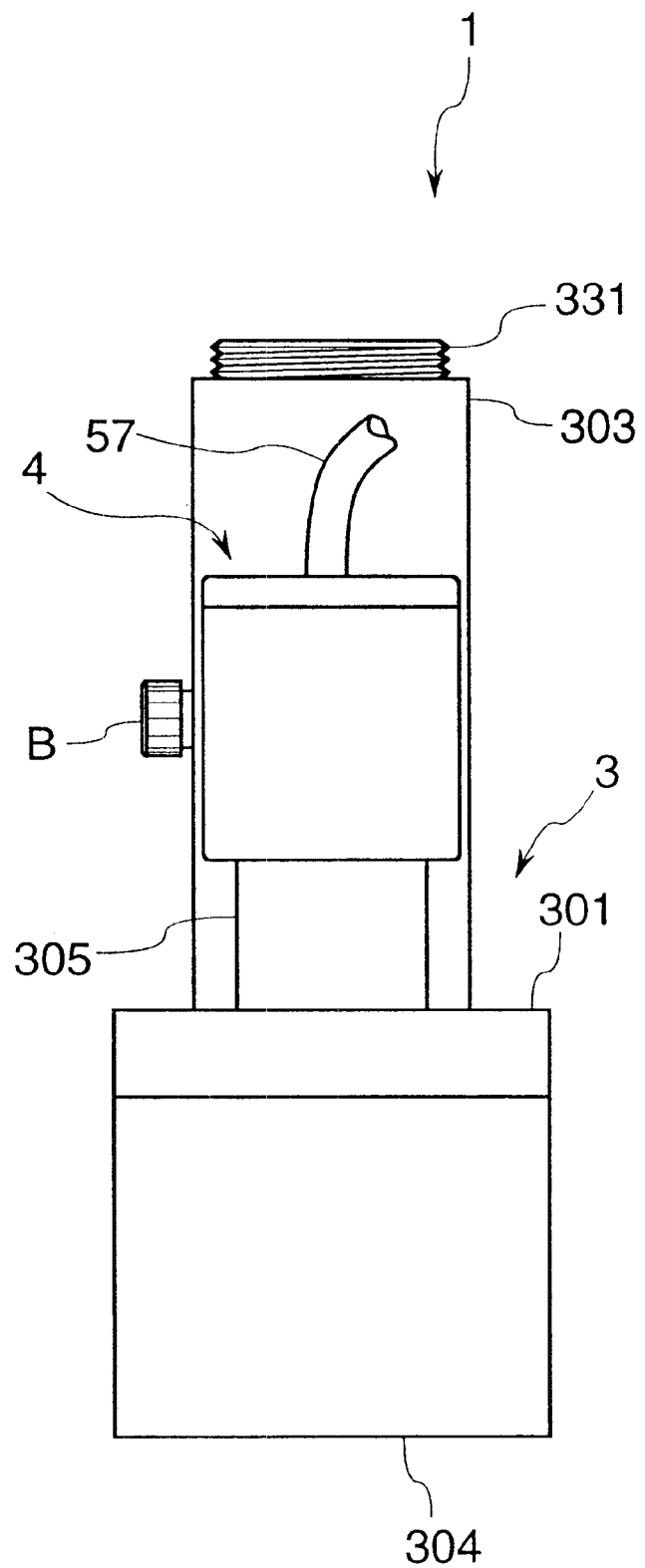
FIG. 15 is a rear view of the unit for inspecting a surface in accordance with the embodiment.
Figure 16:
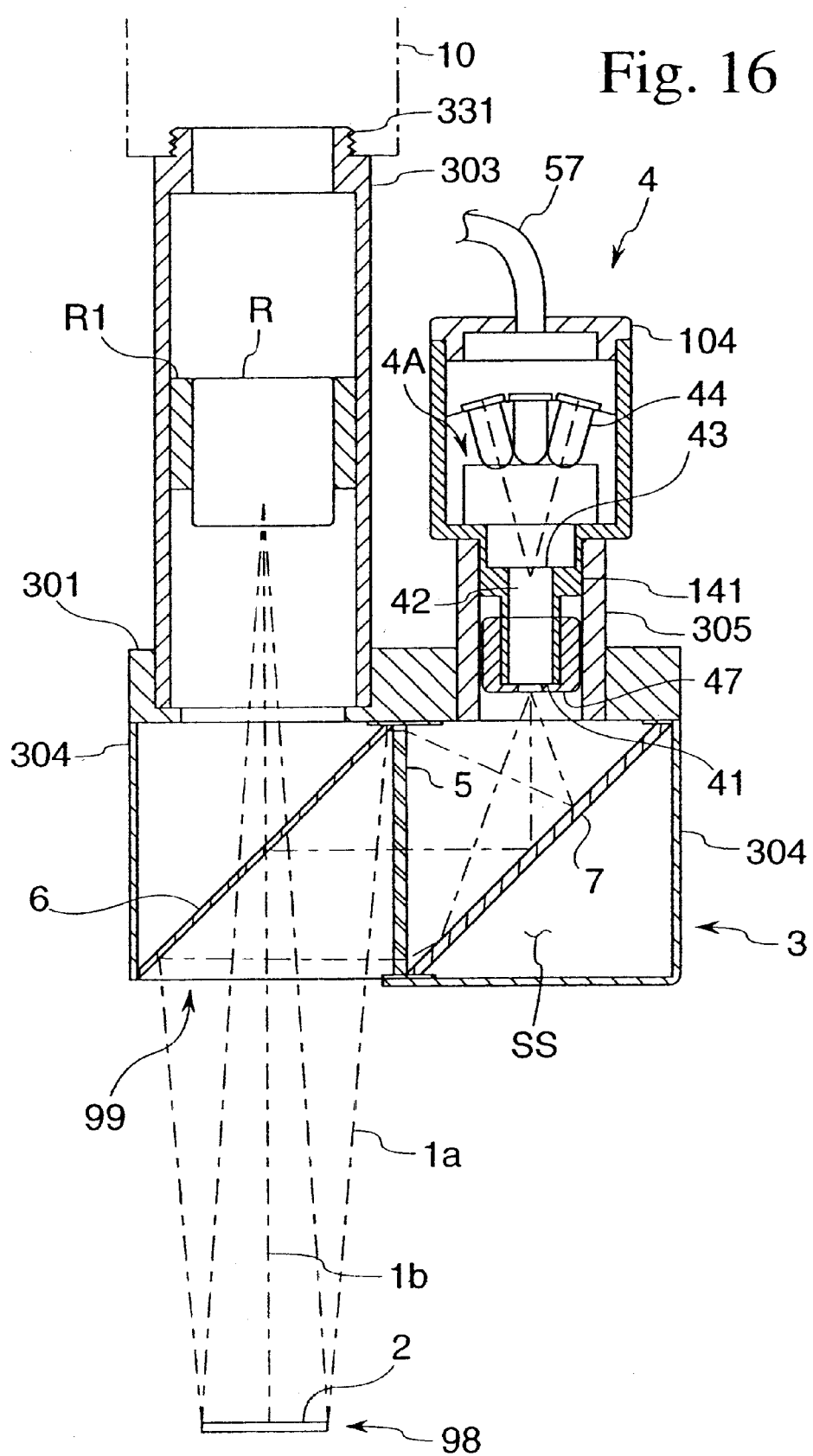
FIG. 16 is a sectional view taken along line A—A in FIG. 15.
Figure 17:
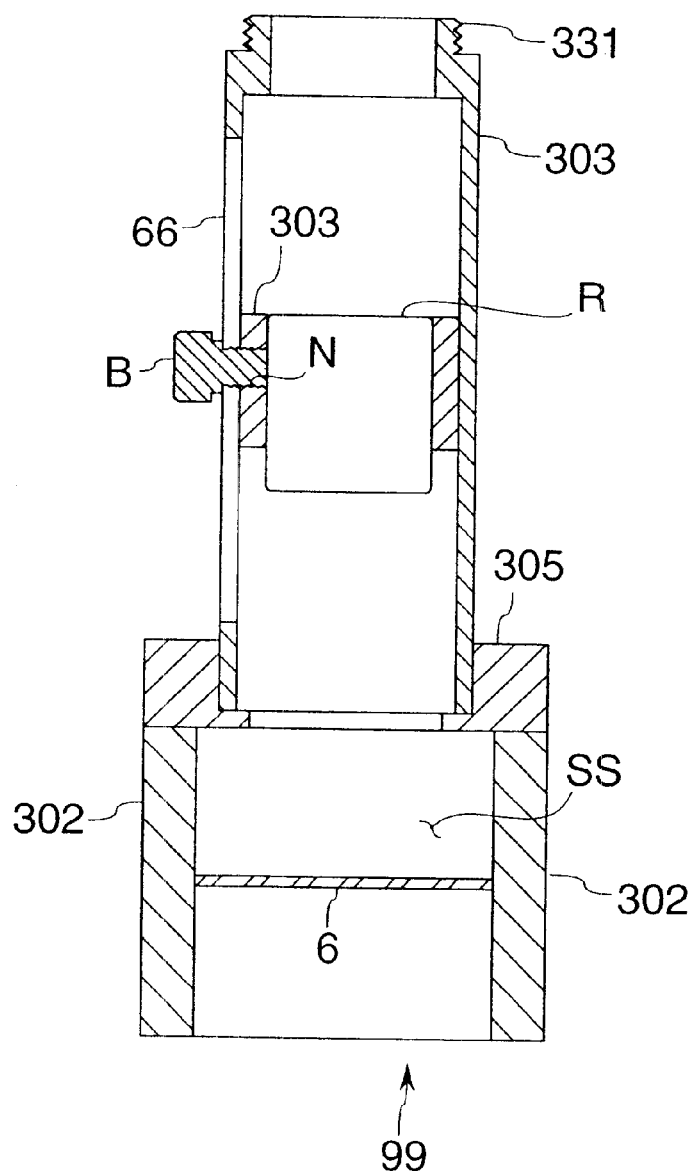
FIG. 17 is a sectional view taken along line B—B in FIG. 14.

The area illuminating element 4B comprises, as shown in FIGS. 11 and 12, a disk-shaped transparent body 141, a disk-shaped supporting plate 142 which is overlapped with one of the face plates of the transparent body 141 and a plurality of LEDs 143 arranged to surround the transparent body 141 so as to illuminate light toward the center of the transparent body 141. The area illuminating element 4B is provided with a through hole 144 which is bored through the center thereof along a direction of thickness and area-illuminates to make the other face plate of the transparent body 141 as an illuminating face. The illuminating face 141b is integrally mounted on the point illuminating element 4A in a posture that the illuminating face 141b is in parallel with the Fresnel lens 5 and as well as faces thereto. More specifically, the supporting plate 142 is opaque and an end face 142a of an opaque side of the supporting plate 142 is provided with a screw hole 142b for mounting. The transparent body 141 is provided with a plurality of concave portions 141c at certain intervals on the outer circumferential face thereof and the LED 143 is embedded into each of the concave portions 141c. The illuminating face 141b is made to be in a condition of a frosted glass so as to area-illuminate uniformly. The LEDs may be spread all over one face plate of the transparent body 141 so as to directly irradiate the light irradiated from these LEDs on the illuminating face instead of embedded around the transparent body 141.

The point illuminating element 4A and the area illuminating element 4B are so made to be switched to illuminate. The point illuminating element 4A is illuminated in order to inspect an specular portion as mentioned above, while the area illuminating element 4B is illuminated in order to inspect a printed surface.

In accordance with the arrangement, other surfaces such as a printed surface besides a specular surface can be inspected by means of the area illuminating element 4B. Especially with the unit, the light irradiated from the illuminating element 4 is promoted to diffuse by passing through the Fresnel lens 5, thereby to improve accuracy of inspection. In this case, it is preferable that the light irradiated from the illuminating element 4 is white and the image capturing unit such as the CCD camera 10 can display in color.

In addition, since a printing state can be inspected with the unit 1 for inspecting a surface, it is possible to conduct a work from manufacturing to inspection in a series of a flow if the unit 1 of this embodiment is arranged to attach to a printing machine which provides printing on back of a specular portion of a CD or the like.

It is needless to say that the arrangement of the illuminating means 4 of this embodiment may be applied to the illuminating means 4 of the first embodiment.

(The Forth Embodiment)

A forth embodiment of the present claimed invention will now be explained with referring to FIGS. 13 through 17. The same reference number is given to the element corresponding to the first, second and third embodiments.

The unit 1 for inspecting a surface is, for example, smaller in size than the unit of the first, second and third embodiment and has fundamentally the same arrangement as that of the first embodiment. More concretely, the unit 1 for inspecting a surface comprises a casing 3 as a body, an illuminating means 4, a total reflecting mirror 7, a Fresnel lens 5, a half mirror 6 and a CCD camera 10 as an image capturing means. Chief differences between the unit of the forth embodiment and that of the first embodiment are; the CCD camera 10 is detachably mount on an outside of the body in this embodiment, and a refracting lens R is arranged near the CCD camera 10 on the optical axis 1b and the refracting lens R is made to slidably move along the optical axis 1b.

More specifically, the casing 3 comprises a rectangular top plate 301, a pair of side plates 302 extending downward from the long sides of the top plate 301, a cylinder body 303 extending from a front side of the top plate 301 to a reverse direction to the side plates 302, namely upward, and a cover 304 which covers a second cylinder body 305 extending upward from anti-front side of the top plate 301 and a space between surrounding edges of the side plates 302 from outside. The cylinder body 303 is in a shape of a cylinder whose both top and bottom ends are open and a lower end portion is embedded in the top plate 301. Generally half portion of a front between the bottom ends of the side plates 302 is so made not to be covered by the cover 304 so as to form an opening 99 at the portion.

The illuminating means 4 is, like each of the above-mentioned embodiments, made of a column-shaped optical transmitting body 42 having a light guiding face 43 at a front end thereof and an illuminating face 41 at a base end thereof, and a point light source element 4A comprising a plurality of LEDs 44 arranged so as to gather the irradiated light on the light guiding face 43 of the column-shaped optical transmitting body 42, both of which are incorporated in a stepped cylinder-shaped box body 104 and so arranged that the light 1a is irradiated from the illuminating face 41. Like the above-mentioned embodiment it is so arranged that light diffusion effect is produced at a overlapped portion by overlapping a plate-shaped light diffusing panel 47 with the illuminating face 41 of the column-shaped optical transmitting body 42.

The illuminating means 4 is so arranged that a smaller portion 141 of a body 104 is supported by the second cylinder body 305 which penetrates the top plate 301 in a direction of thickness in a posture that the illuminating face 41 faces downward, namely the light 1a is irradiated vertically downward.

The total reflection mirror 7 is a plane mirror fixed at an angle of 45 degrees on an anti-front side in a space SS. The total reflecting mirror 7 changes a direction of the light 1a traveling vertically downward and which is irradiated from the illuminating means 4 at 90 degrees so as to make the light 1a travel horizontally toward the front side.

The Fresnel lens 5 is arranged to erect vertically with its face plate facing the front side at a general center of the space SS in the casing 3 at a position so that the optical axis 1b of the light 1a reflected by the total reflecting mirror 7 passes the center of the Fresnel lens S and the light 1a which has passed through the Fresnel lend 5 is refracted so as to converge in a condition of being close to parallel.

The half mirror 6 is a plane mirror which reflects generally half of the irradiated light 1a and through which the remaining half thereof permeates. The half mirror 6 is fixed above the opening 99 in front of the Fresnel lens 5 on the front side in the space SS in a posture in parallel with the total reflecting mirror 7, namely at an angle of 45 degrees.

The CCD camera 10 is releasably mounted on an external thread portion 311 provided at an upper end of the cylinder body 303 in a posture that the light 1a which reflects into the object 98 to be inspected, passes through the half mirror 6 and travels from vertically downward along the cylinder body 303 can be introduced thereinto. The CCD camera 10 is provided with a cord 57 through which a captured image or the like can be output and a connector, which is not shown in drawings, provided at a front end of the cord 57 so as to see the image on a display or the like.

In this embodiment, a refracting lens R is arranged at a middle portion of the cylinder body 303 and the refracting lens R is made to slidably move vertically along the optical axis 1b. More concretely, the refracting lens R is arranged inside the cylinder body 303 through a lens supporting body R1 which is fixed to outer circumference of the refracting lens R, a screw B is passed through a through groove 66 extending vertically and provided on the cylinder body 303 and the screw B is tightened to or loosened from a threaded hole N provided on the lens supporting body R1 so that the refracting lens R can be moved vertically along the optical axis 1b or can be fixed it at a desired position.

In accordance with the arrangement, not only the same effects as that of the first embodiment can be obtained but also it becomes possible to change a range of vision or to focus the refracting lens R by only a slidable movement of the refracting lens R without moving the illuminating means 4 and the CCD camera 10 relatively to the casing 3. In other words, for magnifying the range of vision, a distance between the object to be inspected and the unit is made long and the refracting lens R is moved upward. For reducing the range of vision, a distance between the object to be inspected and the unit is made short and the refracting lens R is moved downward. As mentioned above, the unit has an arrangement in which a number of a portion which should be operated to move is small, thereby to improve efficiency in operation.

Figure 18:
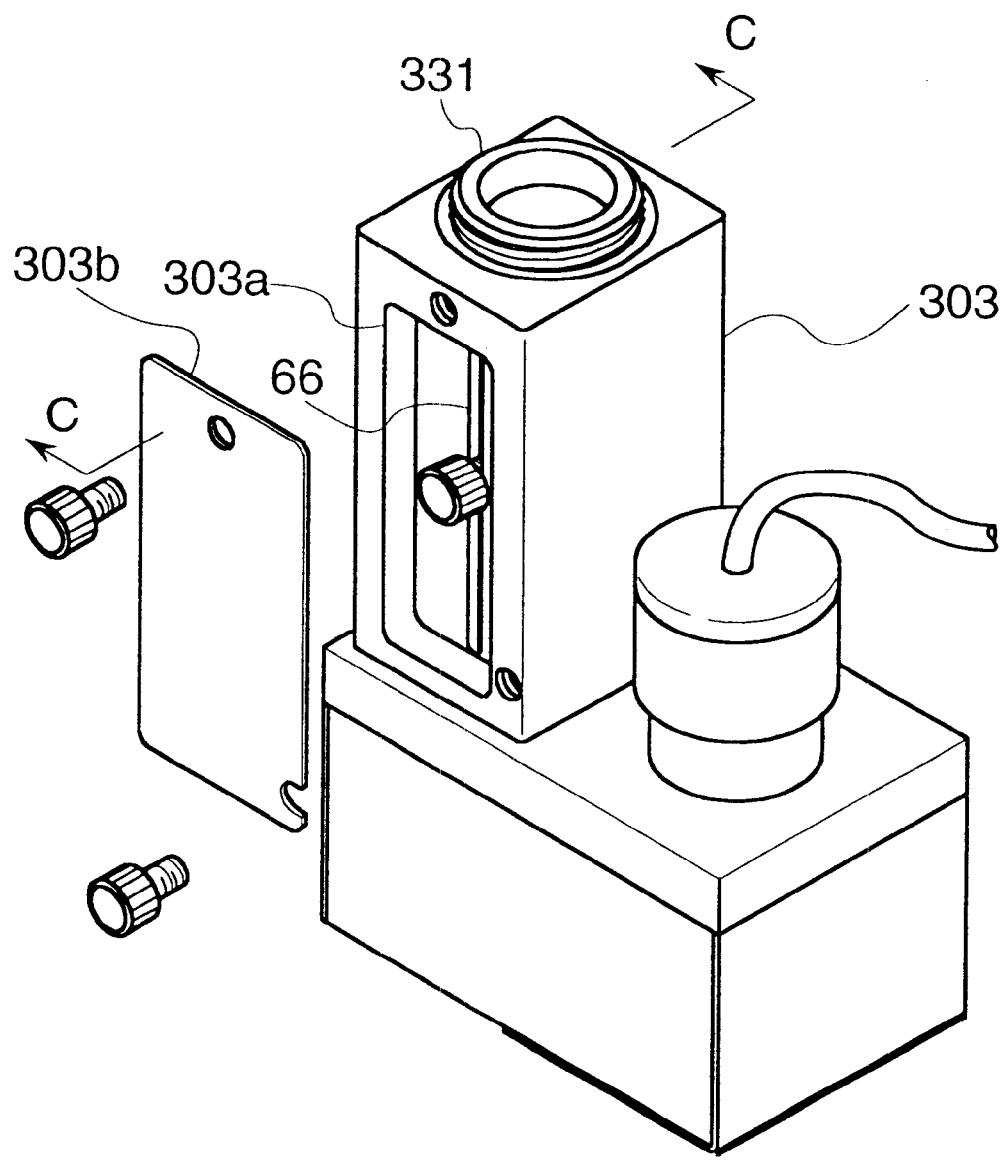
FIG. 18 is a perspective view showing a modified unit for inspecting a surface of the embodiment.
Figure 19:
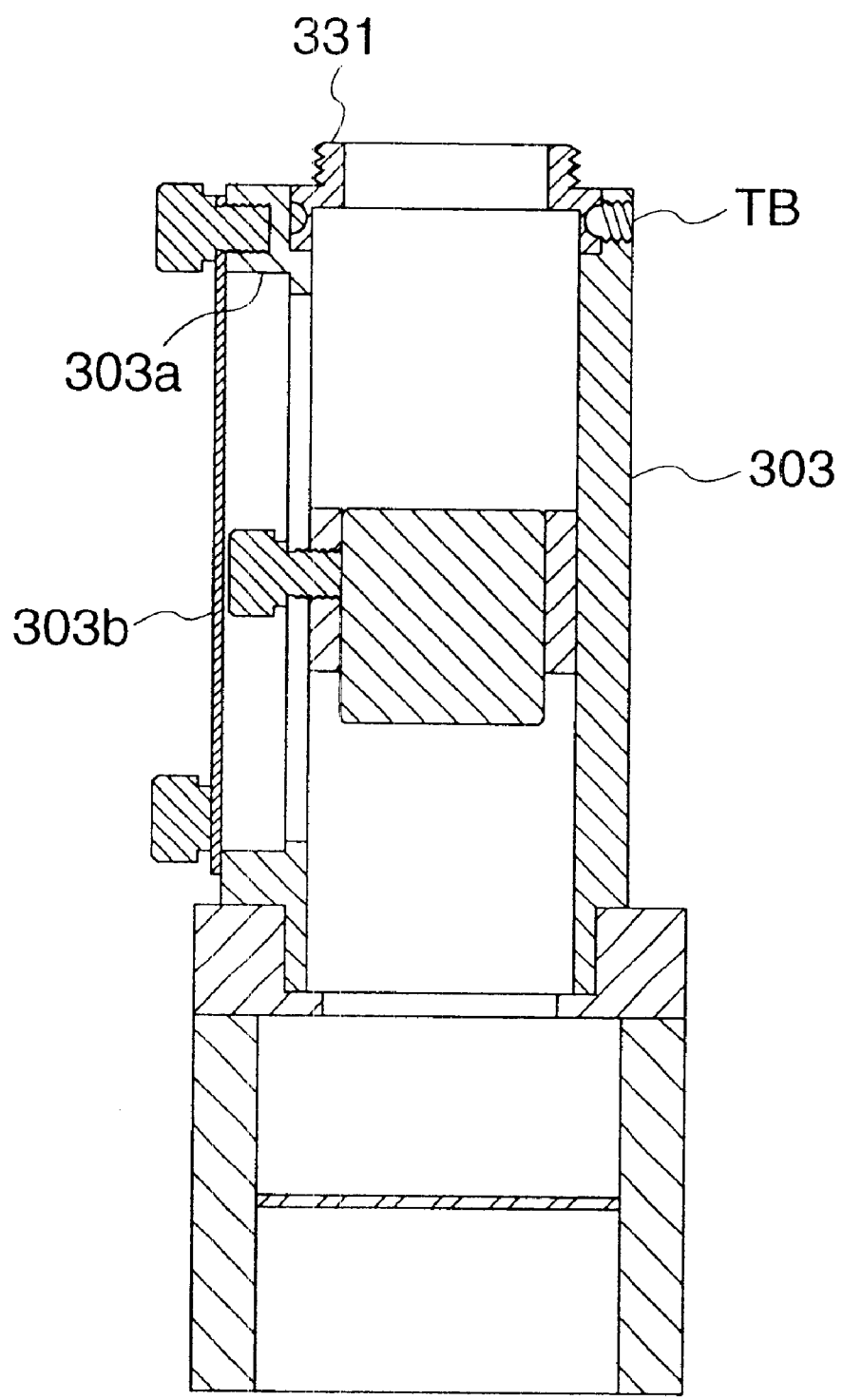
FIG. 19 is a sectional view taken along line C—C in FIG. 18.

FIGS. 18 and 19 show a modified form of the forth embodiment. In the modified form, a cylinder body 303 is provided with a concave portion 303a, a through groove 66 is formed in the concave portion 303a and a cover 303b is provided to cover an opening of the concave portion 303a. With the modified form, light is prevented from coming in through the through groove 66 from outside while the refracting lens R is not prevented from making a sliding movement. Therefore, no bad effect will be produced in inspection. In addition, an external thread 331 provided on the upper end of the cylinder body 303 is so arranged that can be fixed to the cylinder body at an angle arbitrarily by rotating at an axis of the external thread 331. The external thread 331 is fixed with a setscrew TB. This is intended to make it possible to arrange an angle of the CCD camera 10 to the cylinder body arbitrarily when the CCD camera 10 is fixed to the external thread 331.

Figure 20:
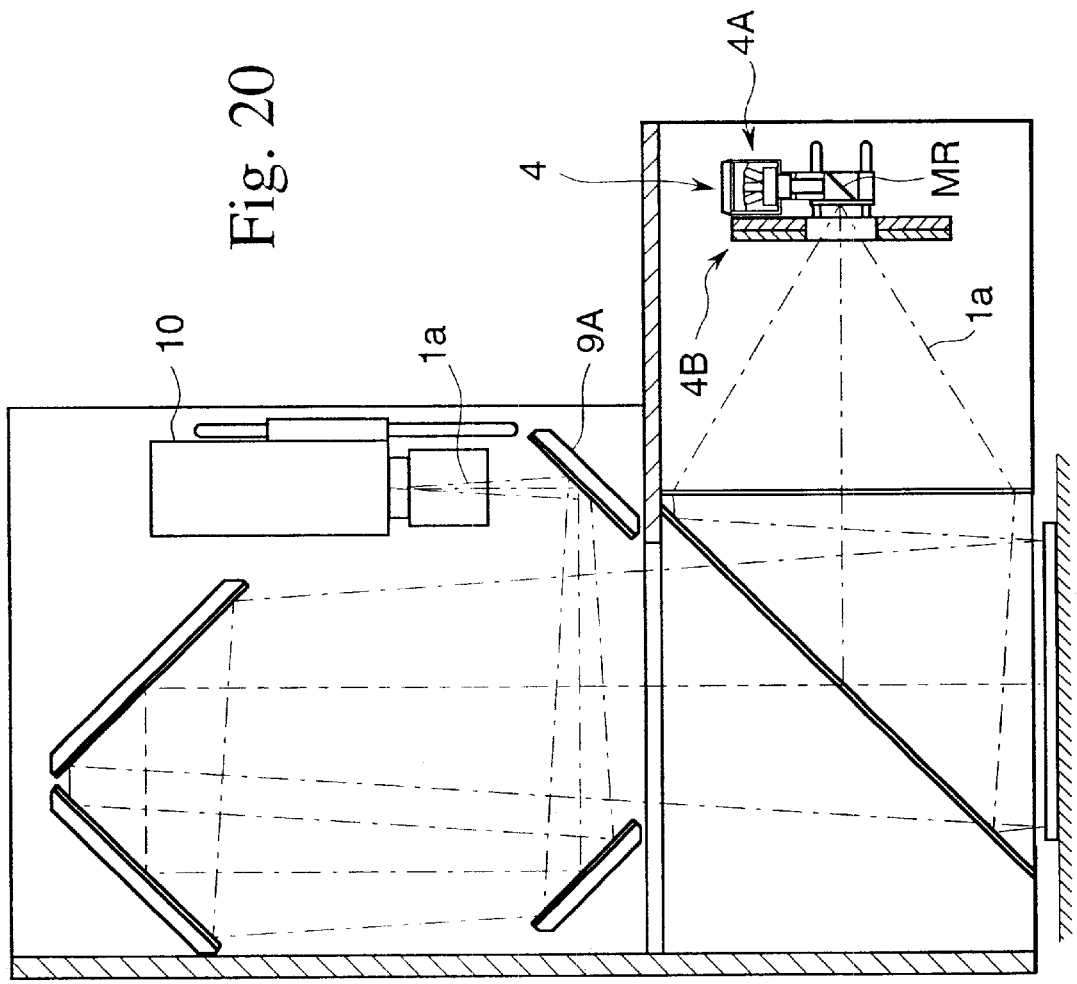
FIG. 20 is a cross-sectional side view showing an internal structure of a unit for inspecting a surface in accordance with the fifth embodiment of the invention.
Figure 21:
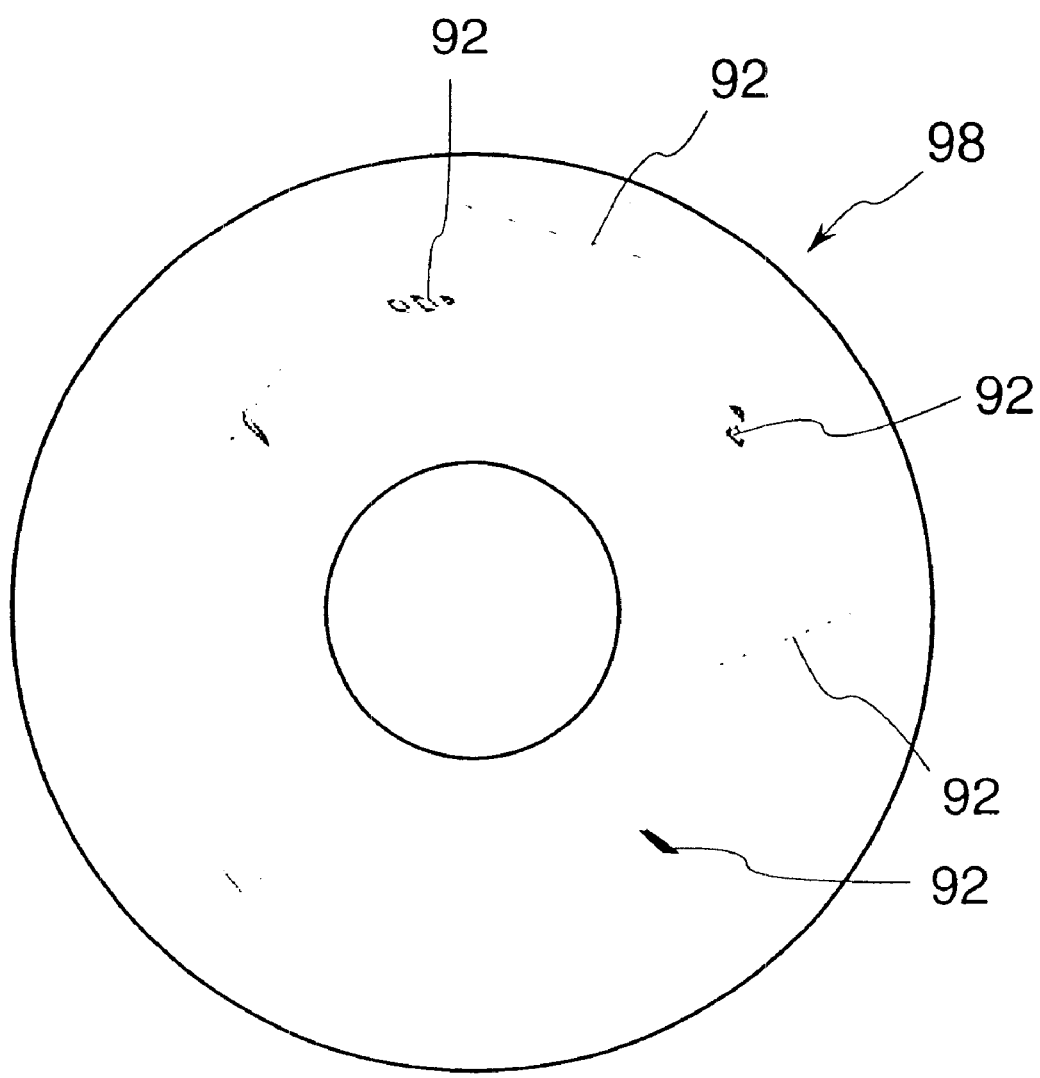
FIG. 21 is an image of a CD taken by a conventional unit for inspecting a surface.

The invention is not limited to the above-mentioned embodiment. For example, if a number of the total reflecting mirror in accordance with the second or third embodiment is increased by one to be an even number, an image captured by the image capturing means is not made to be a mirror image. This will improve workability of inspecting a surface. The arrangement is shown in FIG. 20 as the fifth embodiment. In the fifth embodiment the light 1a introduced into the CCD camera 10 is made to face upward and the CCD camera 10 is placed upright by adding one more total reflecting mirror 9A to the arrangement of the third embodiment. In addition, the point illuminating element 4A is placed upright in a posture that the illuminating face 41 faces downward and the light diffusing panel 47 is arranged at right angles with a traveling direction of the light 1a which is reflected against a reflecting mirror MR to travel horizontal so as to produce light diffusion effect. This makes it possible to downsize a depth of the unit.

The light source may be not only an LED but also an optical fiber. The delustered processing is not limited to a black anodized aluminum.

It is not needless to say that the above-described unit for inspecting a surface can be used upside down so as to place the opening upside and a posture of the unit may be varied according to usage.

Concrete arrangement of other components is not limited to the above-mentioned embodiment, and there may be various modifications without departing from the spirit and essential characteristics thereof.

What is claimed is:

1. A unit for inspecting a surface, which is utilized in inspecting a flaw generated on a specular surface to be inspected or in reading a carved mark on a specular surface to be inspected, characterized by that an illuminating means having a point illuminating element as a point light source or close to a point light source, a Fresnel lens, a half mirror and an image capturing means are supported by a body, wherein light is irradiated from the illuminating means, the light is refracted by the Fresnel lens so as to converge in a condition of being close to parallel, the refracted light by the Fresnel lens is reflected against the half mirror, the reflected light is irradiated on generally whole area of the surface to be inspected and the reflected light is introduced into the image capturing means provided at a position where the light converges, wherein the illuminating means is provided to move along an optical axis of the light irradiated from the illuminating means.

2. The unit for inspecting a surface described in claim 1 and characterized by that the light reflected against the surface to be inspected is introduced into the image capturing means by reflecting light a plurality of times against a plurality of reflecting mirrors provided inside the body.

3. The unit for inspecting a surface described in claim 2 and characterized by that a number of the reflecting mirror provided is an even number.

4. The unit for inspecting a surface described in claim 1, characterized by that the image capturing means can be detachably mounted on outside the body, a refracting lens is arranged both on an optical axis of the light and near the image capturing means, and the refracting lens can be moved slidably along the optical axis.

5. The unit for inspecting a surface described in claim 1, characterized by that the image capturing means is provided to move along the optical axis of the light introduced into the image capturing means.

6. The unit for inspecting a surface described in claim 1 and characterized by that the point illuminating element comprises a column-shaped optical transmitting body having a light guiding fade at one end thereof and an illuminating face at the other end thereof and a plurality of LEDs or photo fibers arranged so as to gather the irradiated light on the light guiding face of the column-shaped optical transmitting body, and is so arranged that the light is irradiated from the illuminating face wherein a light diffusing portion is provided on the illuminating face of the column-shaped optical transmitting body so that light diffusion effect is produced.

7. The unit for inspecting a surface described in claim 1, characterized by that a part or whole of the body is provided with a delustered processing.

8. The unit for inspecting a surface described in claim 2, characterized by that the image capturing means can be detachably mounted on outside the body, a refracting lens is arranged both on an optical axis of the light and near the image capturing means, and the refracting lens can be moved slidably along the optical axis.

9. The unit for inspecting a surface described in claim 3, characterized by that the image capturing means can be detachably mounted on outside the body, a refracting lens is arranged both on an optical axis of the light and near the image capturing means, and the refracting lens can be moved slidably along the optical axis.

10. The unit for inspecting a surface described in claim 2, characterized by that the illuminating means is provided to move along an optical axis of the light irradiated from the illuminating means.

11. The unit for inspecting a surface described in claim 3, characterized by that the illuminating means is provided to move along an optical axis of the light irradiated from the illuminating means.

12. The unit for inspecting a surface described in claim 4, characterized by that the illuminating means is provided to move along an optical axis of the light irradiated from the illuminating means.

13. The unit for inspecting a surface described in claim 4, characterized by that the image capturing means is provided to move along the optical axis of the light introduced into the image capturing means.

14. The unit for inspecting a surface described in claim 4, characterized by that a part or whole of the body is provided with a delustered processing.

15. The unit for inspecting a surface described in claim 6, characterized by that a part or whole of the body is provided with a delustered processing.

16. A unit for inspecting a surface wherein light is irradiated from an illuminating means provided near a focal point of a Fresnel lens, the light is refracted by the Fresnel lens so as to converge, the refracted light by the Fresnel lens is reflected against a half mirror, the light is irradiated on generally whole area of a specular surface to be inspected and the reflected light is introduced into an image capturing means, characterized by the illuminating means comprises a point illuminating element as a point light source or close to a point light source and a ring-shaped area illuminating element arranged to surround the point illuminating element wherein the point illuminating element and the area illuminating element are so arranged to the switched to illuminate.

17. The unit for inspecting a surface described in claim 16 and characterized by that the light reflected against the surface to be inspected is introduced into the image capturing means by reflecting light a plurality of times against a plurality of reflecting mirrors provided inside the body.

18. The unit for inspecting a surface described in claim 9 or 17, wherein the area illuminating means comprises a disk-shaped transparent body, a disk-shaped supporting plate which is overlapped with one of the face plates of the transparent body and a plurality of LEDs arranged to surround the transparent body so as to illuminate light toward the center of the transparent body and is so arranged that a through hole is provided at the center thereof to pass through the light irradiated from the point illuminating element and the other face plate of the transparent body is made to area-illuminate the light as an illuminating face.

19. The unit for inspecting a surface described in claim 17, wherein the area illuminating means comprises a disk-shaped transparent body, a disk-shaped supporting plate which is overlapped with one of the face plates of the transparent body and a plurality of LEDs arranged to surround the transparent body so as to illuminate light toward the center of the transparent body and is so arranged that a through hole is provided at the center thereof to pass through the light irradiated from the point illuminating element and the other face place of the transparent body is made to area-illuminate the light as an illuminating face.

* * * * *

UNITED STATES PATENT AND TRADEMARK OFFICE
CERTIFICATE OF CORRECTION

PATENT NO.    : 6,538,729 B2
DATED         : March 25, 2003
INVENTOR(S)   : Kenji Yoneda It is certified that error appears in the above-identified patent and that said Letters Patent is hereby corrected as shown below:

<u>Column 14,</u>
Line 46, "fade" has been replaced with -- face --;

<u>Column 16,</u>
Line 4, "the" has been replaced with -- be --;
Line 10, "claim 9" has been replaced with -- claim 16 --.

Signed and Sealed this

Ninth Day of September, 2003

JAMES E. ROGAN
*Director of the United States Patent and Trademark Office*